US007494791B2

(12) United States Patent
Goel

(10) Patent No.: US 7,494,791 B2
(45) Date of Patent: Feb. 24, 2009

(54) NANO-PCR: METHODS AND DEVICES FOR NUCLEIC ACID AMPLIFICATION AND DETECTION

(75) Inventor: Anita Goel, Cambridge, MA (US)

(73) Assignee: Nanobiosym, Inc., Medford, MA (US)

( * ) Notice: Subject to any disclaimer, the term of this patent is extended or adjusted under 35 U.S.C. 154(b) by 153 days.

(21) Appl. No.: 11/128,301

(22) Filed: May 13, 2005

(65) Prior Publication Data

US 2006/0019274 A1  Jan. 26, 2006

Related U.S. Application Data

(60) Provisional application No. 60/616,793, filed on Oct. 6, 2004, provisional application No. 60/570,907, filed on May 13, 2004.

(51) Int. Cl.
*C12P 19/34* (2006.01)
*C12Q 1/68* (2006.01)
(52) U.S. Cl. .................. 435/91.2; 435/6; 435/91.1; 435/91.2
(58) Field of Classification Search ................ None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,965,188 A | 10/1990 | Mullis et al. | |
| 5,527,670 A | 6/1996 | Stanley et al. | |
| 5,545,540 A | 8/1996 | Mian | |
| 5,753,439 A * | 5/1998 | Smith et al. | 435/6 |
| 5,824,477 A | 10/1998 | Stanley | |
| 5,939,291 A | 8/1999 | Loewy | |
| 6,017,696 A * | 1/2000 | Heller | 435/6 |
| 6,033,850 A | 3/2000 | Purvis | |
| 6,197,508 B1 | 3/2001 | Stanley | |
| 6,277,605 B1 | 8/2001 | Wijnhoven | |
| 6,291,185 B1 | 9/2001 | Purvis | |
| 6,333,157 B1 | 12/2001 | Miller-Jones | |
| 6,395,489 B1 | 5/2002 | Stanley | |
| 6,408,878 B2 | 6/2002 | Unger et al. | |
| 6,613,527 B1 | 9/2003 | Stanley | |
| 6,696,022 B1 | 2/2004 | Chan et al. | |
| 6,699,713 B2 | 3/2004 | Milanovich et al. | |
| 6,793,753 B2 | 9/2004 | Unger et al. | |
| 6,818,395 B1 | 11/2004 | Quake et al. | |
| 6,911,345 B2 | 6/2005 | Quake et al. | |
| 6,929,030 B2 | 8/2005 | Unger et al. | |
| 6,960,437 B2 | 11/2005 | Enzelberger et al. | |
| 7,033,764 B2 * | 4/2006 | Korlach et al. | 435/6 |

FOREIGN PATENT DOCUMENTS

| | | |
|---|---|---|
| EP | 1384022 | 1/2004 |
| WO | 98/02573 | 1/1998 |
| WO | 00/49176 | 8/2000 |

OTHER PUBLICATIONS

Andricioaei et al., "Dependence of DNA Polymerase Replication Rate on External Forces: A Model Based on Molecular Dynamics Simulations," *Biophysical Journal*, 2004, vol. 87, pp. 1478-1497, Biophysical Society.
Goel et al., "Unifying Themes in DNA Replication: Reconciling Single Molecule Kinetic Studies with Structural Data on DNA Polymerases," *Journal of Biomolecular Structure & Dynamics*, 2002, vol. 19, n. 4, pp. 1-14, Adenine Press.
Goel et al., "Tuning and switching a DNA polymerase motor with mechanical tension," *PNAS*, 2003, vol. 100, n. 17, pp. 9699-9704, National Academy of Sciences.
Goel et al., "Tuning DNA "strings": Modulating the rate of DNA replication with mechanical tension," *PNAS*, 2001, vol. 98, n. 15, pp. 8485-8489, National Academy of Sciences.
Lia et al., "Supercoiling and denaturation in Gal repressor/heat unstable nucleoid protein (HU)-mediated DNA looping," *PNAS*, 2003, vol. 100, n. 20, National Academy of Sciences.
Charvin et al., "Single-molecule study of DNA unlinking by eukaryotic and prokaryotic type-II topoisomerases," *PNAS*, 2003, vol. 100, n. 17, National Academy of Sciences.
Strick et al., "Phase coexistence in a single DNA molecule," *Physica A*, 1999, v. 263, pp. 392-404, Elsevier Science.
Strick et al., "Micro-mechanical measurement of the torsional modulus of DNA," *Genetica*, 1999, vol. 106, pp. 57-62, Springer.
Dessinges et al., "Single-molecule assay reveals strand switching and enhanced processivity of UvrD," *PNAS*, 2004, vol. 101, n. 17, pp. 6439-6444, National Academy of Sciences.
Shaevitz et al., "Backtracking by single RNA polymerase molecules observed at near-base-pair resolution," *Nature*, 2003, vol. 426, pp. 684-687, Nature Publishing Group.
Lang et al., "Combined optical trapping and single-molecule fluorescence," *Journal of Biology*, 2003, vol. 2, n. 1, Article 6, 2003 (published online at jbiol.com/content/2/1/6).
Wang et al., "Force and Velocity Measured for Single Molecules of RNA Polymerase," *Science*, 1998, vol. 282, pp. 902-907, American Association for the Advancement of Science.

(Continued)

*Primary Examiner*—Young J Kim
(74) *Attorney, Agent, or Firm*—Hamilton, Brook, Smith & Reynolds, P.C.

(57) ABSTRACT

Methods, devices, and compositions are described that provide for amplification of nucleic acid sequences without reliance upon temperature cycling, thus freeing the methods from conventional benchtop thermal cycling devices. Denaturation of double stranded nucleic acids, primer annealing, and precision control over primer extension by polymerase can be accomplished by applying stress to a nucleic acid. These methods can provide one ore more benefits over conventional PCR methods including: precision control over the PCR process; generally improved fidelity; improved accuracy over problematic sequences such as GC-rich or tandem repeat regions; greater sequence length; increased reaction yield; reduced experimental time; greater efficiency; lower cost; greater portability; and, robustness to various environmental parameters, such as temperature, pH, and ionic strengths.

82 Claims, 8 Drawing Sheets

OTHER PUBLICATIONS

Perkins et al., "Forward and Reverse Motion of Single RecBCD Molecules on DNA," *Biophysical Journal*, 2004, vol. 86, pp. 1640-1648, Biophysical Society.

Schnitzer et al., "Force production by single kinesin motors," *Nature Cell Biology*, 2000, vol. 2, pp. 718-723, Macmillan Magazines, Ltd.

Neuman et al., "Optical trapping," *Review of Scientific Instruments*, 2004, vol. 75, n. 9, American Institute of Physics.

Perkins et al., "Sequence-Dependent Pausing of Single Lambda Exonuclease Molecules," *Science*, 2003, vol. 301, pp. 1914-1918, American Society for the Advancement of Science.

Lang et al., "Simultaneous, coincident optical trapping and single-molecule fluorescence," *Nature Methods*, 2004, vol. 1, n. 2, pp. 1-7, Nature Publishing Group.

Baumann et al., "Stretching of Single Collapsed DNA Molecules," *Biophysical Journal*, 2000, vol. 78, pp. 1965-1978, Biophysical Society.

Rosenfeld et al., "Stepping and Stretching," *The Journal of Biological Chemistry*, 2003, vol. 278, n. 20, pp. 18555-18556, JBC Papers in Press.

Neuman et al., "Ubiquitous Transcriptional Pausing Is Independent of RNA Polymerase Backtracking," *Cell*, 2003, vol. 115, pp. 437-447, Cell Press.

Abbondanzieri et al., "Direct observation of base-pair stepping by RNA polymerase," *Nature*, 2005, vol. 438, pp. 460-465 (doi:10.1038/nature04268), Nature Publishing Group.

Essevaz-Roulet et al., "Mechanical separation of the complementary strands of DNA," *Proc. Natl. Acad. Sci. USA*, 1997, vol. 94, pp. 11935-11940, The National Academy of Sciences.

Bustamante et al., "Ten years of tension: single-molecule DNA mechanics," *Nature*, 2003, vol. 421, pp. 423-427, Nature Publishing Group.

Li et al., "Rapid spontaneous accessibility of nucleosomal DNA," *Nature Structural & Molecular Biology*, 2005, vol. 12, n. 1, pp. 46-53, Nature Publishing Group.

Gore et al., "Bias and error in estimates of equilibrium free-energy differences from nonequilibrium measurements," *PNAS*, 2003, vol. 100, n. 22, National Academy of Sciences.

Bustamante et al., "The Physics of Molecular Motors," *Acc. Chem. Res.*, 2001, vol. 34, pp. 412-420, American Chemical Society.

Forde et al., "Using mechancial force to probe the mechanism of pausing and arrest during continuous elongation by *Escherichia coli* RNA polymerase," *PNAS*, vol. 99, n. 18, pp. 11682-11687, National Academy of Sciences.

Ritort et al., "A two-state kinetic model for the unfolding of single molecules by mechanical force," *PNAS*, 2002, vol. 99, n. 21, pp. 13544-13548, National Academy of Sciences.

Keller et al., "Relating Single-Molecule Measurements to Thermodynamics," *Biophysical Journal*, 2003, vol. 84, pp. 733-738, Biophysical Society.

Liphardt et al., "Reversible Unfolding of Single RNA Molecules by Mechanical Force," *Science*, 2001, vol. 292, pp. 733-737, American Society for the Advancement of Science.

Davenport et al., "Single-Molecule Study of Transcriptional Pausing and Arrest by *E. coli* RNA Polymerase," *Science*, 2000, vol. 287, pp. 2497-2500, American Society for the Advancement of Science.

Bryant et al., "Structural transitions and elasticity from torque measuremets on DNA," *Nature*, 2003, vol. 424, pp. 338-106, Nature Publishing Group.

Bustamante, "Of torques, forces and protein machines," *Protein Science*, 2004, vol. 13, pp. 3061-3065, Cold Spring Harbor Laboratory Press.

Smith et al., "The bacteriophage phi 29 portal motor can package DNA against a large internal force," *Nature*, 2001, vol. 413, pp. 748-752, Nature Publishing Group.

Bustamante et al., "Single-molecule studies of DNA mechanics,:" *Current Opinion in Structural Biology*, 2000, vol. 10, pp. 279-285, Elsevier Science Ltd.

Johnson et al., "Early Steps of Supported Bilayer Formation Probed by Single Vesicle Fluorescence Assays," *Biophysical Journal*, 2002, vol. 83, pp. 3371-3379, Biophysical Society.

Smith et al., "Self-Diffusion of an Entangled DNA Molecule by Reptation," *Physical Review Letters*, 1995, vol. 75, n. 2, The American Physical Society.

Zhuang et al., "Correlating Structural Dynamics and Function in Single Ribozyme Molecules," *Science*, 2002, vol. 296, pp. 1473-1476, American Society for the Advancement of Science.

Smith et al., "Dynamical Scaling of DNA Diffusion Coefficients," *Macromolecules*, 1996, vol. 29, pp. 1372-1373, American Chemical Society.

Perkins et al., "Relaxation of a Single DNA Molecule Observed by Optical Microscopy," *Science*, 1994, vol. 264, pp. 822-826, American Society for the Advancement of Science.

Quake et al., "The dynamics of partially extended single molecules of DNA," *Nature*, 1997, vol. 388, pp. 151-154, Nature Publishing Group.

Hur et al., "Dynamics and configurational fluctuations of single DNA molecules in linear mixed flows," *Physical Review*, 2002, vol. 66, pp. 011915-1-011915-4, The American Physical Society.

Schroeder et al., "Dynamics of DNA in the Flow-Gradient Plane of Steady Shear Flow: Observations and Simulations," *Macromolecules*, 2005, vol. 38, pp. 1967-1978, American Chemical Society.

Hur et al., "Dynamics of dilute and semidilute DNA solutions in the start-up of shear flow," *J. Rheol.*, 2001, vol. 45, n. 2, pp. 421-450, The Society of Rheology, Inc.

Perkins et al., "Single Polymer Dynamics in an Elongational Flow," *Science*, 1997, vol. 276, pp. 2016-2021, American Society for the Advancement of Science.

Zhuang et al., "Fluroescence quenching: A tool for single-molecule protein-folding study," *PNAS*, 2000, vol. 97, n. 26, pp. 14241-14244, National Academy of Sciences.

Larson, "Hydrodynamics of a DNA molecule in a flow field," *Physical Review*, 1997, vol. 55, n. 2, pp. 1794-1797, The American Physical Society.

Bartley et al., "Exploration of the Transition State for Teriary Structure Formation between an RNA Helix and a Large Structured RNA," *J. Mol. Biol.*, 2003, vol. 328, pp. 1011-1026, Academic Press.

Ha et al., "Ligand-induced conformational changes observed in single RNA molecules," *Proc. Natl. Acad. Sci. USA*, 1999, vol. 96, pp. 9077-9082, National Academy of Sciences.

Schroeder et al., "Effect of Hydrodynamic Interactions on DNA Dynamics in Extensional Flow: Simulation and Single Molecule Experiment," *Macromolecules*, 2004, vol. 37, pp. 9242-9256, American Chemical Society.

Kim et al., "Mg2+-dependent conformational change of RNA studied by fluorescence correlation and FRET on immobilized single molecules," *PNAS*, vol. 99, n. 7, pp. 4284-4289, National Academy of Sciences.

Babcock et al., "Relating the Microscopic and Macroscopic Response of a Polymeric Fluid in a Shearing Flow," *Physical Review Letters*, 2000, vol. 85, n. 9, pp. 2018-2021, The American Physical Society.

Weninger et al., "Single-molecule studies of SNARE complex assembly reveal parallel and antiparallel configurations," *PNAS*, 2003, vol. 100, n. 25, pp. 14800-14805, National Academy of Sciences.

Russell et al., "Exploring the folding landscape of a structured RNA," *PNAS*, 2002, vol. 99, n. 1, pp. 155-160, National Academy of Sciences.

Zhuang et al., "A Single-Molecule Study of RNA Catalysis and Folding," *Science*, 2000, vol. 288, pp. 2048-2051, American Society for the Advancement of Science.

Smith et al., "Single-Polymer Dynamics in Steady Shear-Flow," *Science*, 1999, vol. 283, pp. 1724-1727, American Society for the Advancement of Science.

Bowen et al., "Single Molecule Studies of Synaptotagmin and Complexin Binding to the SNARE Complex," *Biophys.*, vol. 89, pp. 690-702 (*BioFAST*, published on line Apr. 8, 2005, pp. 1-56 (with figures)), The Biophysical Society.

Perkins et al., "Stretching of a Single Tethered Polymer in a Uniform Flow," *Science*, 1995, vol. 268, pp. 83-87, American Society for the Advancement of Science.

Smith et al., "Response of Flexible Polymers to a Sudden Elongational Flow," *Science*, vol. 281, pp. 1335-1340, American Society for the Advancement of Science.

Blanchard et al., "tRNA dynamics on the ribosome during translation," *PNAS*, 2004, vol. 101, n. 35, pp. 12893-12898, National Academy of Sciences.

Perkins et al., "Direct Observation of Tube-Like Motion of a Single Polymer Chain," *Science*, 1994, vol. 264, pp. 819-822, American Society for the Advancement of Science.

Larson et al., "Brownian dynamics simulations of a DNA molecule in an extensional flow field," *J. Rheol.*, 1999, vol. 42, n. 2, pp. 267-304, The Society of Rheology, Inc.

Namasivayam et al., "Light-Induced Molecular Cutting: Localized Reacation on a Single DNA Molecule," *Analytical Chemistry*, 2003, vol. 75, n. 16, pp. 4188-4194, American Chemical Society.

Bockelmann et al., "Unzipping DNA with Optical Tweezers: High Sequence Sensitivity and Force Flips," *Biophysical Journal*, 2002, vol. 82, pp. 1537-1553, Biophysical Society.

Li et al., "DNA molecules and configurations in a solid-state nanopore microscope," *Nature Materials*, 2003, vol. 2, pp. 611-615, Nature Publishing Group.

Butler et al., "Brownian dynamics simulations of a flexible polymer chain which includes continuous resistance and multibody hydrodynamic interactions," *The Journal of Chemical Physics*, 2005, vol. 122, pp. 014901-1-014901-11, American Institute of Physics.

Chou et al., "Integrated Elastomer Fluidic Lab-on-a-chip- Surface Patterning and DNA Diagnostics," *Proceedings of Solid State Sensor and Acutator Workshop*, Hilton Head, Jun. 2000.

Kartalov et al., "Microfluidic device reads up to four consecutive base pairs in DNA sequencing-by-synthesis," *Nucleic Acids Research*, 2004, vol. 32, n. 9, pp. 2873-2879, Oxford University Press.

Filippova et al., "Quantifying Double-Strand Breaks and Clustered Damages in DNA by Single-Molecule Laser Fluorescence Sizing," *Biophysical Journal*, 2003, vol. 84, pp. 1281-1290, Biophysical Society.

Chou et al., "Microfabricated Devices for Sizing DNA and Sorting Cells," *Micro- and Nanofabricated Structures and Devices for Biomedical Environmental Applications*, Paul L. Gourley, Editor, Proceedings of SPIE, vol. 3258, pp. 181-187, 1998.

Chou et al., "Disposable Microdevices for DNA Analysis and Cell Sorting," *Proc. Solid-State Sensor and Acuator Workshop*, Hilton Head, SC, Jun. 8-11, 1998, pp. 11-14.

Fu et al., "An Integrated Microfabricated Cell Sorter," *Anal. Chem.*, 2002, vol. 74, pp. 2451-2457, American Chemical Society.

Meiners et al., "Femtonewton Force Spectroscopy of Single Extended DNA Molecules," *Physical Review Letters*, 2000, vol. 84, n. 21, The American Physical Society.

Reese et al., "Microfabricated Fountain Pens for High-Density DNA Arrays," *Genome Research*, 2003, vol. 13, pp. 2348-2352, Cold Spring Harbor Laboratory Press.

Rolland et al., "Solvent-Resistant Photocurable "Liquid Teflon" for Microfluidic Device Fabrication," *J. Am. Chem. Soc.*, 2004, vol. 126, pp. 2322-2323, American Chemical Society.

Van Dam et al., "Gene Expression Analysis with Universal n-mer Arrays," *Genome Research*, 2002, vol. 12, pp. 145-152, Cold Spring Harbor Laboratory Press.

Gerton et al., "Tip-Enhanced Fluorescence Microscopy at 10 Nanometer Resolution," *Physical Review Letters*, 2004, vol. 93, n. 18, pp. 180801-1-4, The American Physical Society.

Liu et al., A nanoliter rotary device for polymerase chain reaction,: *Electrophoresis*, 2002, vol. 23, pp. 1531-1536, Wiley-VCH Verlag GmbH.

Hong et al., "Integrated nanoliter systems," *Nature Biology*, 2003, vol. 21, n. 10, pp. 1179-1183, Nature Publishing Group.

Hong et al., "A nanoliter-scale nucleic acid processor with parallel architecture," *Nature Biology*, 2004, vol. 22, n. 4, pp. 435-439, Nature Publishing Group.

Thorsen et al., "Dynamic Pattern Formation in a Vesicle-Generating Microfluidic Device," *Physical Review Letters*, 2001, vol. 86, n. 18, The American Physical Society.

Braslavsky et al., "Sequence information can be obtained from single DNA molecules," *PNAS*, 2003, vol. 100, n. 7, pp. 3960-3964, National Academy of Sciences.

Hansen et al., "A robust and scalable microfluidic metering method that allows protein crystal growth by free interface diffusion," *PNAS*, 2002, vol. 99, n. 26, National Academy of Sciences.

Chou et al., "A Microfabricated Rotary Pump," *Biomedical Microdevices*, 2001, vol. 3, n. 4, pp. 323-330, Kluwer Academic Publishers.

Quake et al., "From Micro- to Nanofabrication with Soft Materials," *Science*, 2000, vol. 290, pp. 1536-1540, American Society for the Advancement of Science.

Brody et al., "Significance and statistical errors in the analysis of DNA microarray data," *PNAS*, 2002, vol. 99, n. 20, pp. 12975-12978, National Academy of Sciences.

Thorsen et al., "Microfluidic Large-Scale Integration," *Science*, 2002, vol. 298, pp. 580-584, American Society for the Advancement of Science.

Fu et al., "A microfabricated fluorescence-activated cell sorter," *Nature Biotechnology*, 1999, vol. 17, pp. 1109-1111, Nature America Inc.

Hansen et al., "Microfluidics in structural biology: smaller, faster . . . better," *Current Opinion in Structural Biology*, 2003, vol. 13, pp. 538-544, Elsevier.

Hansen et al., "Systematic investigation of protein phase behavior with a microfluidic formulator," *PNAS*, vol. 101, n. 40, pp. 14431-14436, National Academy of Sciences.

Eyal et al., "Velocity-independent microfluidic flow cytometry," *Electrophoresis*, 2002, vol. 23, pp. 2653-2657, Wiley-VCH Verlag GmbH.

Liu et al., "Solving the "World-to-Chip" Interface Problem with a Microfluidic Matrix," *Analytical Chemistry*, vol. 75, n. 18, pp. 4718-4723, American Chemical Society.

Van Den Broek et al., "DNA-tension dependence of restriction enzyme activity reveals mechanochemical properties of the reaction pathway," *Nucleic Acids Research*, 2005, vol. 33, n. 8, pp. 2676-2684, Oxford University Press.

Munce et al., "Single Cell Analysis on a Microchip Platform using Optical Tweezers and Optical Scissors," in *Micromachining and Microfabrication 2003:, Microfluidics, BioMEMS, and Medical Microsystems*, SPIE 4982, San Jose, CA, Jan. 27-29, 2003, p. 28-36.

Huang, "Microfluidic Devices for Genomic Analysis," A dissertation presented to the faculty of Princeton University in candidacy for the degree of Doctor of Philosophy,—Oct. 2003, pp. 1-95.

Marko et al., "Twist and shout (and pull): Molecular chiropractors undo DNA," *Proc. Natl. Acad. Sci. USA*, 1997, vol. 94, pp. 11770-11772, The National Academy of Sciences.

Rusu et al., "Direct Integration of Micromachined Pipettes in a Flow Channel for Single DNA Molecule Study by Optical Tweezers," *Journal of Microelectromechanical Systems*, 2001, vol. 10, n. 2, pp. 238-245.

Van Oijen et al., "Single-Molecule Kinetics of Exonuclease Reveal Base Dependence and Dynamic Disorder," *Science*, 2003, vol. 301, pp. 1235-1238.

Scherer and Quake Monolithic Integration of Microfluidics and Optoelectronics for Biological Analysis, ARO Grant No. DAAD 19-00-1-0392 DARPA Biofips Report on Standard Form 298, Apr. 15, 2004.

Maier et al, "Replication by a single DNA polymerase of a stretched single-stranded DNA," *PNAS*, 2000, vol. 97, n. 22, pp. 12002-12007, National Academy of Sciences.

Frothingham, "Applications of the Polymerase Chain Reaction to Infectious Disease Diagnosis," *Annals of Saudi Medicine*, 1996, vol. 16, pp. 657-665.

Singh-Zocchi et al., "Single-molecule detection of DNA hybridization," *PNAS*, 2003, vol. 100, n. 13, pp. 7606-7610, National Academy of Sciences.

Ros et al., "Single molecule force spectroscopy on ligand-DNA complexes: from molecular binding mechanisms to biosensor application," *Journal of Biotechnology*, 2004, vol. 112, pp. 5-12, Elsevier.

Michael et al., "Evaluation of Polymerase Chain Reaction for Rapid Diagnosis of Tuberculous Meningitis," *Indian Journal of Tuberculosis*, 2002, vol. 49, pp. 133-137.

Svoboda-Newman et al., "Detection of hepatitis C by RT-PCR in formalin-fixed paraffin-embedded tissue from liver transplant patients," *Diagn. Mol. Pathol.*, 1997, vol. 6, n. 2, pp. 123-129 (Abstract from PubMed), National Library of Medicine.

Quint et al., "Reliability of Methods for Hepatitis B Virus DNA Detection," *Journal of Clinical Microbiology*, 1995, vol. 33, n. 1, pp. 225-228, American Society for Microbiology.

Lai et al., "Microsatellite mutations during the polymerase chain reaction: mean field approximations and their applications," *Journal of Theoretical Biology*, 2003, vol. 224, pp. 127-137, Elsevier Ltd.

Zimmerman et al., "DNA stretching on functionalized gold surfaces," *Nucleic Acids Research*, 1994, vol. 22, n. 3, pp. 492-497, Oxford University Press.

Zovarova et al., "New specificity and yield enhancer of polymerase chain reactions," *Nucleic Acids Research*, 2000, vol. 28, n. 13, pp. i-iv, Oxford University Press.

Ladoux et al., "Direct imaging of single-molecules: from dynamics of a single DNA chain to the study of complex DNA-protein interactions," *Science Progress*, 2001, vol. 84, n. 4, pp. 267-290.

Shivashankar et al., "RecA polymerization on double-stranded DNA by using single-molecule manipulation: The role of ATP hydrolysis," *PNAS*, 1999, vol. 96, pp. 7916-7921, National Academy of Sciences.

Wong et al., "Deformation of DNA molecules by hydrodynamic focusing," *J. Fluid Mech.*, 2003, vol. 497, pp. 55-65, Cambridge University Press.

Wulte, G.J.L. et al., "Single-molecule studies of the effect of template tension on T7 DNA polymerase activity," Nature, 404:103-106 (2000).

Smith, S.B. et al., "Direct Mechanical Measurements of the Elasticity of Single DNA Molecules by Using Magnetic Beads," Science, 258:1122-1126 (1992).

Strick, T. et al., "Twisting and Stretching Single DNA Molecules," Progress in Biophysics & Molecular Biology, 74:115-140 (2000).

Smith, S.B. et al., "Overstretching B-DNA: The Elastic Response of Individual Double-Stranded and Single-Stranded DNA Molecules," Science, 271:795-799. (1996).

Rouzina, I. et al., "Force-Induced Melting of the DNA Double Helix,"Biophysical Journal, 80:882-893 (2001).

* cited by examiner

FIGURE 6A
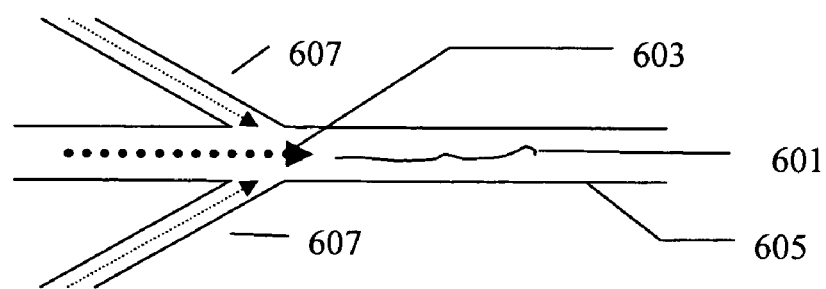
FIGURE 6B
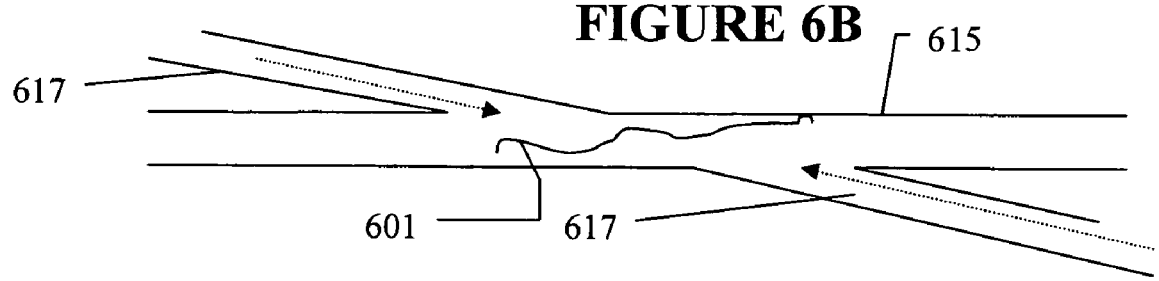
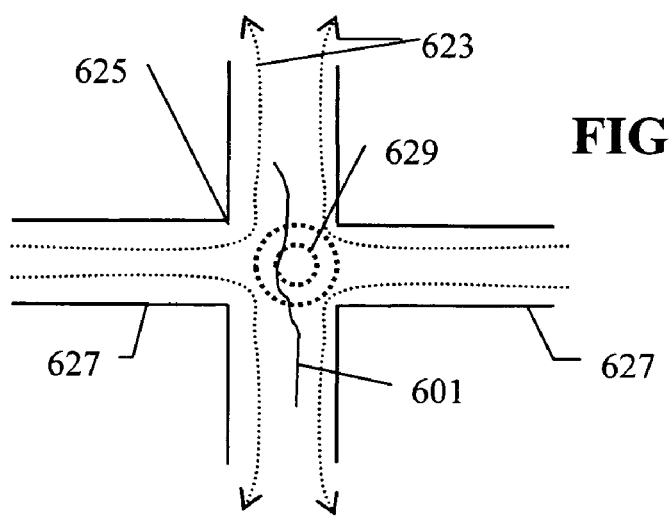
FIGURE 6C

NANO-PCR: METHODS AND DEVICES FOR NUCLEIC ACID AMPLIFICATION AND DETECTION

CONTINUING APPLICATION DATA

This application claims benefit of U.S. Provisional Application No. 60/570,907, filed May 13, 2004, and U.S. Provisional Application No. 60/616,793, filed Oct. 6, 2004, each of which is incorporated by reference herein in its entirety.

FIELD OF THE INVENTION

The invention relates to amplification and detection of nucleic acids. In particular embodiments, the invention provides improved methods, devices, and materials for performing the polymerase chain reaction.

BACKGROUND OF THE INVENTION

The polymerase chain reaction (PCR) has become the conventional technique used to amplify specific DNA or RNA sequences. U.S. Pat. No. 4,683,202, issued Jul. 28, 1987 to Mullis and U.S. Pat. No. 4,683,195, issued Jul. 28, 1987 to Mullis et al. describe the basic PCR technique. Since the first disclosure of the PCR method, it has had a profound effect on the practice of biotechnology and biomedical science. More than a thousand subsequently-issued U.S. patents reference one or both of these disclosures.

Typically, the amplification of a DNA sequence is performed by first selecting and obtaining two oligonucleotide primers complementary ends of a target DNA sequence. The primers, a polymerase enzyme, a mixture of the four common nucleotide triphosphates, various salts and buffers are mixed with the target DNA which is heated above about 90° C. to denature the DNA, separating the target double-stranded DNA into single-stranded DNA templates. Annealing (i.e. sequence-specific hybridization or binding) of the primers to the ends of the DNA templates is promoted by slowly cooling the reaction mixture to less than about 60° C. The temperature is then raised above about 70° C. for a period of replication, a process also known as primer extension. The polymerase reads each DNA template strand in the 3' to 5' direction, synthesizing a complementary strand from the ends of the primers in the 5' to 3' direction. This completes one cycle of DNA amplification, which creates starting material for a new cycle. With each complete cycle of denaturation, primer annealing, and primer extension, the process generates an exponentially increasing ($2^n$) number of copies of the original, target DNA sequence. To begin a new cycle, the reaction mixture is again heated above 90° C. to denature the double-stranded product into single-stranded DNA templates. The primer annealing and extension steps are then repeated.

This basic PCR amplification scheme, together with various extensions and modifications, enables many different methods for the manipulation and detection of nucleic acids, including for example diagnostic and forensic assays, which require the creation of a threshold amount of DNA from a small initial sample. PCR technology is used, for example, in infectious and genetic disease monitoring, DNA and RNA sequencing, gene expression studies, drug development, and forensic fingerprinting. This has become the standard technology for the detection, identification, and quantification of viral and bacterial pathogens. Several PCR-based diagnostic tests are available for detecting and/or quantifying pathogens, for example, including: HIV-1, which causes AIDS; hepatitis B and C viruses, which can cause liver cancer; human papillomarvirus, which can cause cervical cancer; RSV, which is the leading cause of pneumonia and bronchiolitis in infants; *Chlamydia trachomatis* and *Neisseria gonorrhoeae*, which can lead to pelvic inflammatory disease and infertility in women; cytomegalovirus, which can cause life-threatening disease in transplant patients and other immuno-compromised people; and, *Mycobacterium tuberculosis*, which causes cough and fatigue in its active state and can irreversibly damage infected organs. However, despite addressing needs in numerous areas, current PCR and PCR-based technologies still suffer from several substantial limitations.

Limitations of Conventional PCR and PCR-Based Technologies

Fidelity: Accuracy on normal sequences limits conventional PCR. For example, Taq, a thermostable polymerase commonly used for DNA amplification, exhibits an error rate of approximately $1 \times 10^{-4}$ errors/base pair during PCR. This means that the PCR amplification of a 400 base pair DNA sequence will randomly introduce approximately 40,000 errors among all molecules in the PCR product over 20 cycles.

Accuracy on difficult target sequences (e.g. GC rich or repeat sequences) is an even more significant limitation of conventional PCR and PCR-based technologies. The error rate for conventional polymerase enzymes such as Taq, depends strongly on the target nucleotide sequence. For example, when the sequence is G+C rich (as seen for example in the 5' regulatory region of the chicken avidin gene), PCR with Taq is oftentimes not a viable process. Likewise, simple repeating sequences, such as trinucleotide repeats (AGC)n or other tandem repeats (A)n, can increase Taq's error rate to $1.5 \times 10-2$ errors per repeat sequence. See, Shinde et al., Nucleic Acids Research, 31:974. For this reason, several patents have been issued for polymerases that have been genetically engineered to have incrementally higher fidelity (i.e. lower error rates). These include Hi-Fidelity and Phusion Polymerases.

Length Limitations: The length of the target sequence to be amplified also limits current PCR techniques. Although a few reports have claimed amplification of sequences up to 10 to 20 kilobases, this is highly unusual and quite difficult in routine practice. Moreover, PCR amplification of long target templates is only possible on a limited set of well-behaved DNA sequences. The practical upper-limit for fairly routine and cost-effective amplification of DNA on well-behaved sequences is about 300 to 400 bases in length and is generally reduced for sequences having high G-C content.

Limited Amplification: Current PCR techniques are also limited in the number of amplification cycles that can be carried out in a reaction mixture. Repeated heating and cooling cycles result in progressive enzyme degradation, which limits the factor by which starting material can be amplified. Conventional PCR amplification can rarely be extended beyond 30-35 cycles.

Robustness: Conventional PCR typically requires significant volumes of reagents, bulky equipment (e.g., thermal cyclers), substantial human labor (e.g., tedious optimizations), and minimum amounts of starting material, each of which contributes to making conventional PCR a costly and time-consuming process. Current PCR techniques typically take from several hours for normal sequences to several days to weeks for difficult sequences or long template. Conventional PCR requires a significant amount of time to cycle and equilibrate the temperature of the reaction mix. Moreover, time-consuming optimizations can be required in order to reliably amplify targets that are less than ideal.

Tightly controlled conditions (e.g., temperature, pH, and buffer ingredients) are required for performance of conventional PCR techniques. Additionally, various contaminants can interfere with PCR amplification by directly inhibiting or interfering with polymerase enzymes used to copy the target DNA or RNA. This further limits the quality of starting material that can be used for amplification and places additional requirements on the level of purity that must be obtained by DNA or RNA extraction techniques before the amplification steps can be reliably performed. The performance environment of conventional PCR is generally limited to laboratories, and is rarely practicable in remote locations, doctor's offices, at the patient's bedside, or out in the field.

Sensitivity and Specificity of Diagnostics: The sensitivity of PCR-based diagnostic and forensic kits and assays depends on the overall yield, accuracy, robustness, and target length achievable in a PCR reaction. The above-mentioned limitations in performance parameters of current PCR set limits on the minimum amount of starting DNA or RNA necessary in order to reliably carry out PCR amplification. This, in turn, limits the sensitivity of any pathogen detection system, diagnostic, or forensic kits or assays that rely upon conventional PCR or PCR-based technologies. The specificity of a PCR-based diagnostic, forensic, or pathogen detection system depends critically on the accuracy with which DNA can be amplified and read as well as the length of the target DNA or RNA that can be reliably amplified and identified.

For these and other reasons, current generation PCR-based technologies and detection systems are generally limited with respect to overall speed, efficiency, cost-effectiveness, and scope of use. Incremental improvements to conventional PCR methods and devices have been proposed with respect to some of the isolated performance parameters described above. For example, Tso et al. discloses a PCR microreactor for amplifying DNA using microquantities of sample fluid in U.S. Pat. No. 6,613,560, issued Sep. 2, 2003. Alternatives to high temperature DNA denaturation have also been proposed. For example, Purvis disclosed a method of electrochemical denaturation of double-stranded nucleic acid in U.S. Pat. No. 6,291,185, issued Sep. 18, 2001. Stanley discloses another method of electrochemical denaturation of nucleic acids in U.S. Pat. No. 6,197,508, issued Mar. 6, 2001. Dattagupta et al. have disclosed a method of using primers to displace the DNA strand from the template in U.S. Pat. No. 6,214,587, issued Apr. 10, 2001. Mullis, supra, suggested the use of helicase enzymes for separating DNA strands.

In view of the limitations of conventional PCR, and despite the proposal of various incremental improvements, there remains a need in the art for improved methods, devices, and compositions for the amplification, manipulation, sequencing, and detection of nucleic acids.

SUMMARY OF THE INVENTION

The methods and apparatuses described herein provide a breakthrough technology to perform PCR. The technology described herein also permits PCR to be performed without reliance upon thermal cycling. The technology may be applied at a wide range of ambient temperatures or using controlled temperature. It is possible to exercise precise control when desired during replication and amplification, thereby enabling substantial improvements in a number of performance parameters. Dubbed "Nano-PCR™," this technology introduces a new paradigm in PCR-based detection and amplification of nucleic acids.

BRIEF DESCRIPTION OF THE DRAWINGS

FIGS. 6A-6C illustrate exemplary methods of and arrangements of elements of a reaction chamber for applying tension to a DNA strand suspended in a fluid velocity gradient.

DETAILED DESCRIPTION OF EMBODIMENTS OF THE INVENTION

Definitions

Figure 1A:
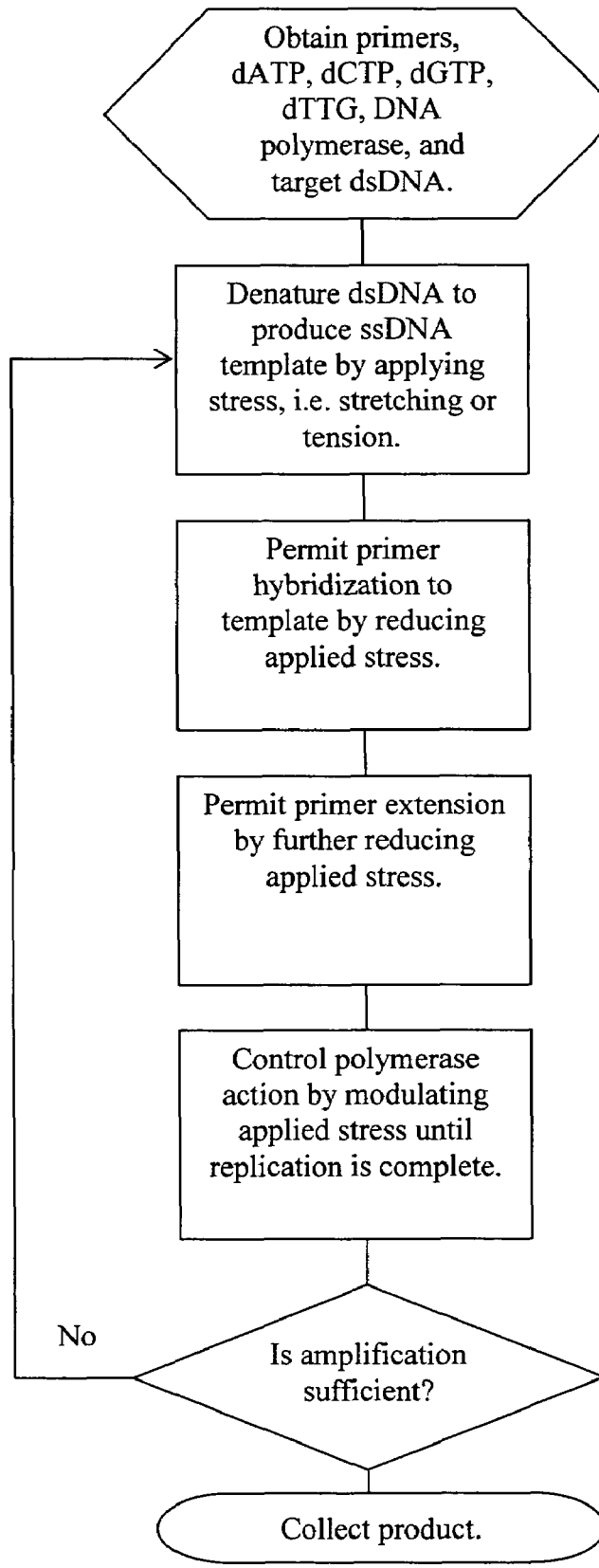
FIGS. 1A and 1B illustrate exemplary flow charts of PCR methods that do not rely on temperature cycling.

The terms "nucleic acid," "polynucleotide," and "oligonucleotide" are used herein to include a polymeric form of nucleotides of any length, including, but not limited to, ribonucleotides or deoxyribonucleotides. There is no intended distinction in length between these terms. Further, these terms refer only to the primary structure of the molecule. Thus, in certain embodiments these terms can include triple-, double- and single-stranded DNA, as well as triple-, double- and single-stranded RNA. They also include modifications, such as by methylation and/or by capping, and unmodified forms of the polynucleotide. More particularly, the terms "nucleic acid," "polynucleotide," and "oligonucleotide," include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from Anti-Virals, Inc. Corvallis, Oreg., as Neugene) polymers, and other synthetic sequence-specific nucleic acid polymers providing that the polymers contain nucleobases in a configuration which allows for base pairing and base stacking, such as is found in DNA and RNA.

As used herein, "primer" refers to a single-stranded polynucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically is at least 7 nucleotides long and, more typically range from 10 to 30 nucleotides in length. Other primers can be somewhat longer such as 30 to 50 nucleotides long. PCR primers are typically about 20-30 base pairs long and are chosen to be complementary to one strand upstream (i.e., 5' to 3') of the target sequence and the opposite strand downstream (i.e., 3' to 5') of the sequence. The 5' ends of the primers define the ends of the amplified PCR product. Primers may contain approximately the same GC content as AT content and no long stretches of any one base. Furthermore, the primers should not contain structures that are substantially complementary to one another. This insures that "primer dimer" formation or other secondary structure does not occur. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target DNA to which a primer hybridizes. The term "primer pair" means a set of primers including a 5' "upstream primer" that hybridizes with the complement of the 5' end of the DNA sequence to be amplified and a 3' "downstream primer" that hybridizes with the 3' end of the sequence to be amplified.

As used herein, the term "complementary" means that one nucleic acid is identical to, or hybridizes selectively to, another nucleic acid molecule. Selectivity of hybridization exists when hybridization occurs that is more selective than total lack of specificity. Typically, selective hybridization will occur when there is at least about 55% identity over a stretch of at least 14-25 nucleotides, alternatively at least 65%, at least 75%, or at least 90%. In one alternative embodiment, one nucleic acid hybridizes specifically to the other nucleic acid. See M. Kanehisa, Nucleic Acids Res. 12:203 (1984).

A primer that is "perfectly complementary" has a sequence fully complementary across the entire length of the primer and has no mismatches. The primer is typically perfectly complementary to a portion (subsequence) of a target sequence. A "mismatch" refers to a site at which the nucleotide in the primer and the nucleotide in the target nucleic acid with which it is aligned are not complementary. The term "substantially complementary" when used in reference to a primer means that a primer is not perfectly complementary to its target sequence; instead, the primer is only sufficiently complementary to hybridize selectively to its respective strand at the desired primer-binding site.

As used herein, a "probe" is a nucleic acid capable of binding to a target nucleic acid of complementary sequence through one or more types of chemical bonds, usually through complementary base pairing, usually through hydrogen bond formation, thus forming a duplex structure. A probe binds or hybridizes to a "probe binding site." A probe can be labeled with a detectable label to permit facile detection of the probe, particularly once the probe has hybridized to its complementary target. A label attached to the probe can include any of a variety of different labels known in the art that can be detected by chemical or physical means, for example. Labels that can be attached to probes include, but are not limited to, radio-isotopes, fluorophores, chromophores, gold particles, quantum dots, mass labels, electron dense particles, magnetic particles, spin labels, molecules that emit chemiluminescence, electrochemically active molecules, enzymes, cofactors, and enzyme substrates. Probes can vary significantly in size. Some probes are relatively short. Generally, probes are at least 7 to 15 nucleotides in length. Other probes are at least 20, 30 or 40 nucleotides long. Still other probes are somewhat longer, being at least 50, 60, 70, 80, 90 nucleotides long. Yet other probes are longer still, and are at least 100, 150, 200 or more nucleotides long. Probes can be of any specific length that falls within the foregoing ranges as well.

A "thermophilic DNA polymerase" is a thermostable DNA polymerase enzyme having an optimum temperature at which it functions, which is higher than 40° C. Oftentimes, the optimum temperature for the function of a thermophilic DNA polymerase ranges from about 50° C. to 80° C., or 60° C. to 80° C. These heat stable enzymes were introduced to provide more robustness to the repeated cycles of heating and cooling the enzyme during conventional PCR.

A "difficult sequence" refers to sequences on which a polymerase enzyme has a tendency to slip, make mistakes or stop working. Examples of difficult sequences include sequences of several residues (e.g. segments of 6, 9, 12, 15, or 30 base pairs or longer) having greater than about 50% G and C base pairs that are called GC-rich sequences, sequences containing tandem repeat segments, polyrepeat sequences such as poly-A sequences, trinucleotide repeat regions as found in sequences associated certain diseases like Huntington's, and other such problematic sequences.

Overview of the Conventional Polymerase Chain Reaction (PCR)

To perform the standard thermal cycling polymerase chain reaction using a thermophilic (i.e. heat stable) DNA polymerase, one typically executes the following steps: 1) prepare a cocktail containing a PCR buffer, a dNTP mixture, a primer pair, a DNA polymerase, and doubly-deionized water in a tube; 2) add the DNA to be amplified to the tube 3) place the tube in a temperature block of a thermal cycler (e.g. Perkin-Elmer™ 9600 or 9700 PCR Thermal Cycler) 4) Program the thermal cycler with specific reaction conditions (e.g. a period for thermal denaturation of double-stranded DNA by heating to above about 90° C. for about 1 to 2 minutes, a period of annealing by slowly cooling to about 50 to 65° C. for 2 min, and a period for polymerization, also called primer extension, by heating to about 70 to 75° C. for a few minutes) that are to be repeated for about 25 to 35 cycles. Executing the method produces about a $2^n$ fold amplification of the starting material, where n is the total number of cycles of amplification that are carried out.

While some limitations of conventional PCR stem from how the conventional technique is typically carried out, several limitations in the performance parameters stem directly or indirectly from the reliance on thermal cycling. Overall reaction yield, amplification efficiency, sensitivity, robustness, and portability are each, for instance, restricted by thermal cycling. The Nano-PCR™ methods overcome not only limitations due to thermal cycling but also several that are inherent to typical implementation of conventional PCR.

Nano-PCR™

Nano-PCR™ methods and apparatuses can dramatically extend the detection and amplification capabilities of the polymerase chain reaction by breaking through several limitations imposed by conventional approaches. Table 1 compares typical performance parameters of current PCR with Nano-PCR™.

TABLE 1

| Performance parameters of current PCR vs. Nano-PCR ™ |||
| --- | --- | --- |
| Performance Parameters | Current Generation PCR | Nano-PCR ™ Methods and Devices |
| Accuracy-normal sequences | Typical error rate of about $1 \times 10^{-4}$ errors/base pair. | Error rates of less than about $1.0 \times 10^{-7}$ errors/base pair or better can be achieved. |
| Accuracy when replicating problematic sequences (GC | Typical error rate of about $1.5 \times 10^{-2}$ errors/repeat sequence. | Error rates of less than about $1.0 \times 10^{-3}$ errors/repeat sequence can be |

TABLE 1-continued

Performance parameters of current PCR vs. Nano-PCR ™

| Performance Parameters | Current Generation PCR | Nano-PCR ™ Methods and Devices |
|---|---|---|
| rich or repeating sequences) | | achieved with precision control of the replication process. |
| Length of amplified sequence | Typically limited to about 300-400 base pairs. | Can amplify extended sequences of up to 20,000 base pairs or more. |
| Overall reaction yield | Reagent and polymerase degradation generally limits amplification to about 30-35 cycles. | Reagents can survive more than 100 cycles of DNA amplification. |
| Cost | Thermal cycler generally costs more than about $4,000. | Small, relatively inexpensive devices can be manufactured to perform Nano-PCR ™. |
| Overall PCR process time | Can require several hours to days. | Can be performed in less than 1 hour |
| Portability | Performed in bench top devices that are restricted to laboratory settings. | Can be performed in a portable hand-held device. |
| Robustness | Requires tightly controlled operational conditions i.e. temperature, pH. Need Highly Pure starting material. | Allows for temperature and pH variations. Can work with a broader range of starting materials. More tolerant to possible contaminants and less sophisticated extraction methods for preparation of starting material. |
| Sensitivity | Typically requires more than 1000 polynucleotides/ml analyte. | Requires less than 10 polynucleotides/ml analyte. |
| Specificity | Rate of false positives in diagnostic kits can exceed 15%. | Rate of false positives in diagnostic kits can be much less than 12.5%. Improved specificity decreases need for costly post-processing and bioinformatics steps used in confirming the sequence of the target DNA or RNA. |

The common denominator of PCR and PCR-based technologies practiced to date has been the use of thermal cycling to sequentially denature DNA, anneal primers, and then extend primers via a polymerase enzyme. The methods described herein, dubbed Nano-PCR™, and apparatuses for performing those methods utilize the application of controlled amounts of force or stress to the nucleic acid molecules to provide new alternatives to thermal cycling for implementing DNA or RNA amplification. As used herein, applying stress to a nucleic acid includes direct and indirect application of force to a nucleic acid that tends to stretch or elongate the nucleic acid. As examples, stress can be applied to a nucleic acid by direct application of mechanical tension, by hydrodynamic stresses in a fluid flow, or electromagnetic fields, whether acting on the nucleic acid molecules themselves and/or on surfaces, substrates, or particles and the like that are bound to the nucleic acid. In many applications, Nano-PCR™ can break through one or more of the limitations that have traditionally restricted the performance and scope of conventional PCR.

Cycling of Mechanical Tension

The application of controlled tension to nucleic acids provides not only an alternative to thermal denaturation of double-stranded DNA (dsDNA) but also a unique capability to precisely control each step of the PCR process. Nano-PCR™ introduces a new approach to amplification of DNA or RNA by exploiting the effects of precisely controlled forces, such as mechanical, hydrodynamic, or electromagnetic stresses on the DNA/RNA molecule and/or on the polymerizing enzyme.

Increasing temperature of solution comprising a DNA molecule and increasing stress on a DNA molecule produce analogous results. Thus, a polymerase reaction cycle can be initiated by increasing tension applied to a DNA template to above about 65 pN to denature the DNA. A step corresponding to the annealing of primers can be effected by slowly decreasing tension on the DNA template to below about 50 pN to allow primers to anneal to the template. Tension in the DNA template can then be adjusted within about 0 to about 30 pN during extension of the primer via enzymatic polymerization in order to control the progress, rate and/or accuracy of the replication. As with thermal cycling in conventional PCR, cycling of stress can be repeated in a pre-programmed cycle in Nano-PCR™ methods.

Figure 1B:
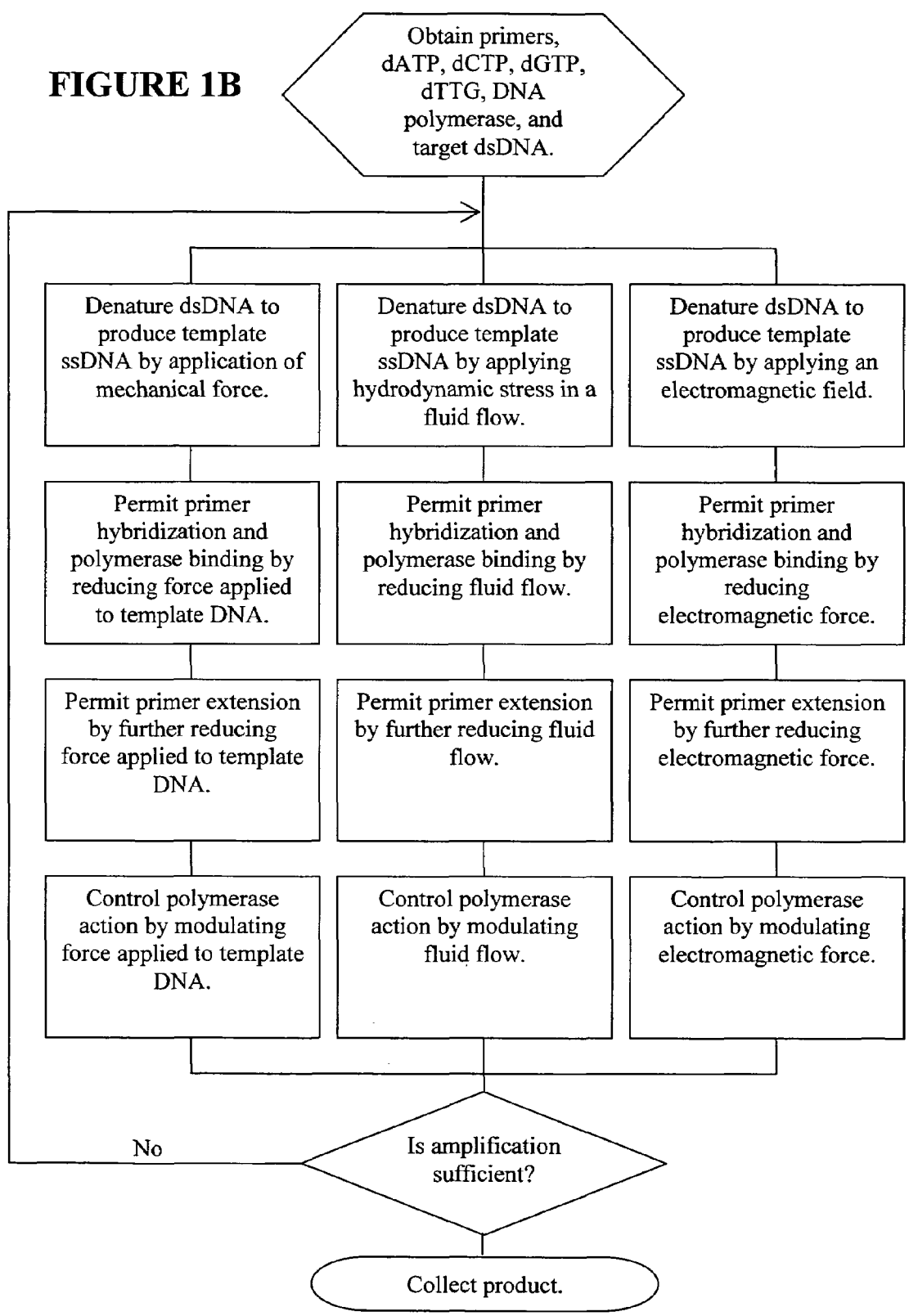

In the examples below, various modes by which these methods can be put into practice are described. Hydrodynamic stresses and/or electric fields applied to the nucleic acid molecules, like mechanical tension can be cycled to perform Nano-PCR™ without reliance on thermal cycling. Of course, although Nano-PCR™ methods can be performed without any temperature cycling, this is not to say that control of temperature will not be advantageous in some embodiments as more fully discussed below. FIGS. 1A and 1B show exemplary flow diagrams for Nano-PCR™ methods. It will be appreciated that alterations and additions to the basic protocol will be made as appropriate for specific tasks such as sequencing, cloning, mutagenesis, mutation screening, and pathogen detection, etc.

At room temperature and standard buffer conditions, application of tension above about 65 pN to double-stranded DNA can cause denaturation (i.e. melting) into single stranded DNA (ssDNA). As used herein, "room temperature" is understood to be a temperature within the normal range of comfortable laboratory temperatures, generally about 20-22° C. A theoretical model of the force-induced melting of DNA at room temperature has been described by Ioulia Rouzina and Victor A. Bloomfield ("Force-Induced Melting of the DNA Double Helix 1. Thermodynamic Analysis" *Biophys J.,* 80:882-93, 2001; and, "Force-Induced Melting of the DNA Double Helix. 2. Effect of Solution Conditions" *Biophys J.,* 80:894-900, 2001). Using the equations of Rouzina and Bloomfield as described herein, it is possible for one of ordinary skill to determine a precise level of tension that will melt a primer in a manner analogous to conventional melting point temperature calculations.

Slowly decreasing the applied tension below about 65 pN in the presence of primer oligonucleotides can permit the selective binding of the primers to template DNA in a manner analogous to slowly cooling denatured DNA below the melting point temperature of a primer in a thermal cycler. Accordingly, during a primer annealing step, tension applied to a nucleic acid template strand can be slowly reduced from an amount that causes dsDNA to melt to an amount that permits primer annealing. It may also be desirable to maintain tension on a DNA strand at a level that substantially inhibits polymerase action, for example at about 30 pN or greater but below about 50 pN, until unbound primer is flushed from the reaction chamber to minimize non-specific binding and non-specific primer extension.

The application of tension to a nucleic acid template in the range from about 0 to about 30 or 35 pN can be used to slow the rate of polymerase activity. The exact speed of the enzyme depends on various factors, including the ambient temperature or ambient concentrations of polymerase and/or nucleotide triphosphate substrates. Tension greater than about 35-45 pN at room temperature promotes the natural proofreading exonuclease activity of the polymerase enzyme.

An exemplary embodiment of a Nano-PCR™ method can comprise: (a) providing a sample of double-stranded DNA (dsDNA) containing a target sequence, one or more oligonucleotide primers, for example a pair of primers complementary to the 3' ends of the target sequence and its complement; at least four different nucleoside triphosphates (i.e. ATP, CTP, GTP, TTP); and a DNA polymerase; (b) denaturing the dsDNA into single-stranded DNA (ssDNA) template strands using a non-thermally-driven process, for example by the application of tension sufficient to cause dsDNA to melt (e.g. tension greater than about 65 pN) to the dsDNA; (c) controlling the non-thermally-driven process to promote hybridization of primers to complementary template strands, for example, where tension was used to denature the dsDNA, by reducing the tension applied to the ssDNA; (d) permitting the DNAp to extend the primers to form dsDNA; and, (e) repeating steps (b-d) until a desired amount of DNA sequence amplification is obtained.

The use of a "non-thermally driven process" in the methods described herein means, for example, that dsDNA denaturation is not accomplished solely through an increase in temperature above the melting temperature of dsDNA, but rather that a physical or mechanical force is exerted on the nucleic acid that does not rely on temperature. The non-thermally driven process may comprise applying tension to the DNA strand, for example by direct application of mechanical force, by fluid flow, by application of an electric field, and/or by the action of one or more denaturing agents. As described herein, the effect of such a force may be affected by temperature so that it may be desirable in a given circumstance to control and optionally to modulate the temperature during one or more steps of the methods.

A target sequence to be amplified can be contained in isolated DNA or in a mixture of nucleic acids and can be contained on complementary strands of equal or unequal lengths. A method may also include starting with a composition comprising RNA and producing a DNA template using reverse transcriptase or a similar method. A target sequence may alternatively be provided on a single stranded nucleic acid, rendering step (b) unnecessary in the first cycle. The reaction components of step (a) can be combined at the start of the procedure or may be introduced separately as needed. Optionally, reaction components can also be removed from the reaction chamber during certain steps. For example, nucleoside triphosphates (NTPs) may be introduced during or prior to step (d) and the primers may be introduced during or prior to step (c) and unbound primers may be flushed from the chamber before the primer extension (replication) step. Further, in various embodiments of the method, tension in the range of about 0-45 pN, about 0-35 pN, or about 0 to 20 pN can be applied to template DNA strands during step (d). In such embodiments, the amount of tension applied to the template strands during step (d) can optionally be varied over time. The amount of tension applied to the template strands in step (d) can varied according to the known or estimated progress of the polymerase in relation to positions of difficult or error prone subsequences, such as G-C rich segments (e.g. segments containing greater than about 50% G-C base pairs, or greater than about 70% G-C base pairs) or the positions of segments containing repeating sequences.

Accuracy of Nano-PCR™ over Normal and "Difficult" Sequences

When tension is applied to the template DNA during the primer extension step, a polymerase can be induced to "reverse direction" and the exonuclease activity of the polymerase can predominate. It will be appreciated that at the atomic scale and over times on the order of a single polymerase/exonuclease step, the process is stochastic. However, when considered from an average over the time scale of several steps the polymerase is seen to exhibit sustained exonuclease activity when the applied tension is greater than a threshold that can be theoretically predicted for a given temperature and solution conditions.

By applying a modulated amount of tension to template DNA during the primer extension step in an amount below the threshold at which the exonuclease activity of a polymerase becomes predominant, e.g, below about 35 to 45 pN at room temperature and normal PCR solution conditions, more preferably in the range of about 10 to 30 pN, Nano-PCR™ can provide substantially increased accuracy of replicating DNA over conventional PCR. Furthermore, this effect can be achieved over those sub-sequences that are difficult using conventional PCR methods. The amount of tension applied to a template DNA strand can be adjusted in the range of about 0 to 45 pN, about 0 to 35 pN, or about 0 to 20 pN over time during the primer extension off a template that contains a mixture of more and less problematic segments. For example, according to a map of the sequence, tension may be increased as necessary to a level below about 35 pN to promote increased accuracy over difficult regions and then be carefully decreased to permit faster processing over less problematic segments. The length of the template strand is changed during the primer extension. In some variations of the methods, it is possible to adjust the tension on the template in direct response to the changes in length of the template strand so as to calibrate the applied tension precisely according to the progress of the polymerization reaction and the particular location of the "difficult" subsequences. In embodiments where it is not practical to directly monitor the progression of the polymerase, the position of the polymerase can be estimated by multiplying the elapsed time by the known rate of replication for the polymerase at the applied amount of tension.

Thus Nano-PCR™ permits accurate replication of not only normal target templates but also difficult sequences (e.g. GC rich DNA, tandem repeat, microsatellite or trinucleotide repeat DNA) to be replicated and amplified with substantially increased accuracy relative to conventional PCR. As an example, where one of the highest fidelity polymerases currently available (e.g. Phusion Enzyme) is used in conventional thermally-driven PCR, error rates of approximately $4.0 \times 10^{-7}$ errors/base pair are observed in favorable cases, that is, only on well-behaved sequences. By contrast Nano-PCR™ methods as described herein can produce an error rate less than about $1.0 \times 10^{-7}$ errors/base pair, less than $5.0 \times 10^{-8}$ errors/base pair, $1.0 \times 10^{-8}$ errors/base pair, $5.0 \times 10^{-9}$ errors/base pair, $1.0 \times 10^{-9}$ errors/base pair, $5.0 \times 10^{-10}$ errors/base pair, or even $1.0 \times 10^{-10}$ errors/base pair. Furthermore the methods described herein can permit the efficient amplification of oligonucleotide fragments having a GC content higher than 50 percent, 60 percent, 70 percent, 75 percent., or even 80 percent or 85 percent.

In certain cases, oligonucleotide fragments contain a section of repeating base pair units at least eight base pairs in length (e.g., AAAAAAAA, GCGCGCGC). The error rate for conventional PCR is increased in such cases, usually approaching $1.0 \times 10^{-2}$ errors/base pair. The present methods of Nano-PCR™ provide for the amplification of repeating base pair units with an error rate less than about $1.0 \times 10^{-3}$ errors/base pair. Under certain conditions, error rates less than $1.0 \times 10^{-4}$ errors/base pair, $1.0 \times 10^{-5}$ errors/base pair, $1.0 \times 10^{-6}$ errors/base pair, or $1.0 \times 10^{-7}$ errors/base pair can be achieved. These low error rates may also be obtained where the repeating base pair unit is at least 10 base pairs in length, at least 15 base pairs in length, or at least 20 base pairs in length. In the methods described herein, such results can also be obtained over microsatellite regions, polymerase slippage regions, and other tandem repeat regions, which are difficult sequences when using conventional PCR methods.

Amplification Efficiency

Where amplification efficiency is defined by the equation $N_1=N_2(1+Y)^n$, and $N_1$ is the number of product copies, $N_2$ is the number of template oligonucleotide copies, n is the number of cycles and Y is the efficiency, efficiencies greater than 80 percent are achieved. Under certain conditions, amplification efficiencies greater than 85 percent, 90 percent, 95 percent, 96 percent, 97 percent, 98 percent, or even 99 percent can be achieved. Such amplification efficiencies can also be obtained where the GC content of the oligonucleotide fragment is greater than 55 percent, 60 percent, 65 percent, 70 percent or even 75 percent. Amplification efficiencies greater than 50 percent can be achieved where the GC content of an oligonucleotide fragment is greater than 50 percent, 55 percent, 60 percent, 65 percent or 70 percent. Efficiencies greater than 60 percent, 70 percent, 80 percent, 90 percent, 95 percent, 97 percent, or even 99 percent can be observed. In conventional PCR, these high GC-rich regions are amplified and sequenced with the addition of various denaturing agents, including but not limited to sodium hydroxide, TMA chloride, TMA oxalate, TMA acetate, TMA hydrogen sulfate, ammonium chloride, benzyldimethylhexadecylammonium chloride, HTA bromide, HTA oxalate, betaine monohydrate, DMSO, and formamide, and the like. In certain embodiments of Nano-PCR™, efficient amplification is also seen using methods as described herein in the absence of such polymerase chain reaction additives.

Robustness and Adaptability

Conventional PCR methods generally rely on precise control and cycling of temperature. Further, conventional PCR methods can require additional factors such as various denaturing agents and tedious optimizations. However, the use of tension cycling to drive amplification as described herein enables a much higher degree of precision and control over the PCR process than allowed by thermal cycling alone. Moreover, the methods described herein can function under a wide range of temperature conditions, limited only by factors such as the range of temperatures under which a chosen polymerase can function and the melting point temperature of the primer/template bond at a given tension.

Of course, it will be appreciated that temperature can affect the rate and accuracy of polymerase enzymes and the melting of DNA under tension. Generally, the amount of tension required to melt dsDNA is decreased with increasing temperature. As a rough guide, from about to 0 to 20° C., up to about 75 pN can be required to melt dsDNA. At about 60° C., the amount of tension required to denature dsDNA can be about 45 pN. The melting tension decreases to about 7 pN at just below the free DNA melting point.

Although it is generally not necessary, it may be advantageous to control the temperature during one or more steps of the methods depending on requirements of an individual application. For example, the temperature of the reaction mixture can be maintained at a temperature that optimizes the accuracy, polymerization rate, and/or tension response of a chosen DNA polymerase, that increases or decreases the amount of tension required to achieve DNA melting, or that is otherwise advantageous because of the individual device or working environment. Unless otherwise desired, the temperature can be generally constant, and the entire process can be performed at or near normal room temperature. Unless otherwise indicated, the examples herein are described using amounts of tension that will be appropriate at room temperature. One of ordinary skill will readily be able to adjust the tension applied to the DNA template for higher or lower temperatures.

Through the application of even small amounts of tension, thermal cycling temperatures no longer impose a limitation on the temperature at which the PCR reaction must be carried out. By applying a tension of about 7 to 45 pN, for example, one can decrease the temperature at which double-stranded DNA denatures by up to about 30 degrees C. Adjusting the amount of tension applied to DNA enables performance of PCR at temperatures well below the amount required for denaturation in conventional PCR. This effect permits PCR using low amplitude thermal cycling. For example, a method can comprise a denaturation step in which an amount of force less than about 65 pN is applied in concert with an increase in the temperature of the solution to less than about 90° C., alternatively less than about 80° C.

The methods and apparatuses described herein may be carried out or operated at temperatures below 90° C. Oligonucleotide denaturation steps, for instance, can be conducted at below 80° C., 70° C., 60° C., 50° C., 40° C., 30° C., or even 25° C. Annealing steps can be conducted below 50° C., 45° C., 40° C., 35° C., 30° C., or even 25° C. Furthermore, polymerization steps can be conducted below 70° C., 60° C., 50° C., 40° C., 30° C., or even 25° C.

Similarly, pH and ionic strength of the solution in which the DNA is immersed can affect the tension-induced melting curves of DNA. Accordingly, by adjusting the levels of force applied to DNA in the methods, Nano-PCR™ permits using a wider range of pH and ionic strength solution conditions to carry out the PCR process than in conventional PCR. Similarly, all these and additional parameters can affect tension control of primer extension. The methods described herein can be adjusted for and even take advantage of these effects. Thus Nano-PCR™ methods can be more robust to a wider range of temperature, ionic strengths, pH and buffer conditions in general, which means that it can be performed in a wider range of situations, demanding less stringent extraction and purification of the starting DNA or RNA material, and can be more resistant to various contaminants and enzyme inhibitors that typically restrict the scope of conventional PCR. In preferred implementations, the presence of contaminating substances can be removed by flushing the sample as part of the Nano-PCR™ process. For example, an unpurified DNA sample containing contaminants can be introduced into a Nano-PCR™ device, the DNA is retained in the reaction chamber, e.g. by any of the means described herein for retaining DNA for the controlled application of stress. The contaminants are flushed out of the reaction chamber and reagents are flushed in. This can provide substantial robustness to the Nano-PCR™ process, permitting rapid accuracte amplification in environments that are unfavorable to conventional PCR.

Nano-PCR™ Using Direct Application of Mechanical Force

Nano-PCR™ methods can be performed utilizing various methods to directly apply mechanical tension to DNA strands as a non-thermally-driven process that can provide for DNA denaturation and/or precise control of the activity of DNA polymerase. There are several different ways to apply tension to a double-stranded oligonucleotide. For example, DNA strands may be anchored in an array to a movable element, to individually controllable elements, or to particles that can be manipulated.

Figure 2A:
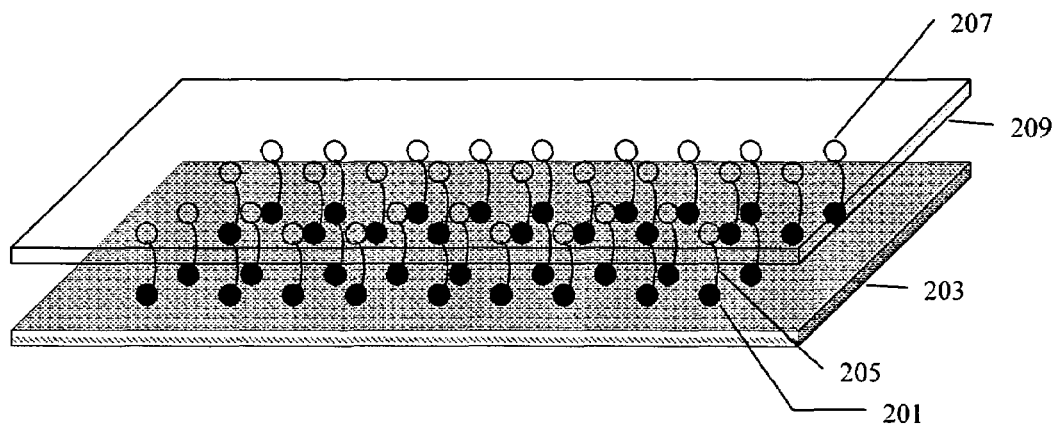
FIGS. 2A-2C illustrate exemplary methods of and arrangements of elements of a reaction chamber for applying tension to a DNA strand anchored between opposed surfaces.
Figure 2B:
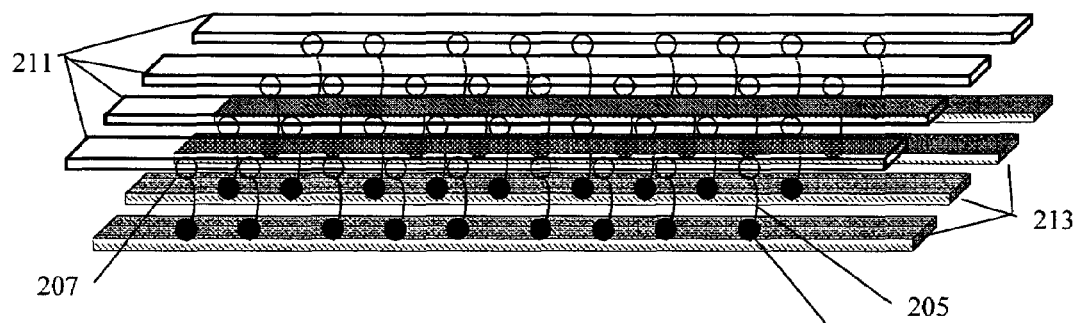
Figure 2C:
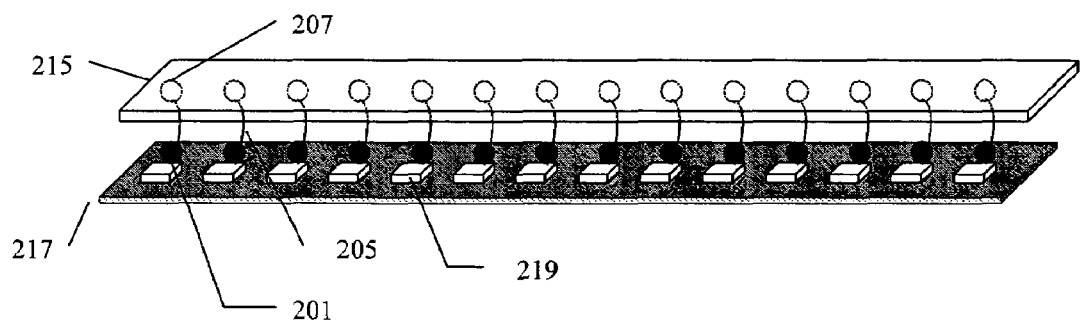

Using Opposed Coated Surfaces:

As an example, the process can be performed using nucleic acids anchored to opposed coated surfaces, generally as illustrated in FIGS. 2A-2C: Coated surfaces are prepared by attaching a first complexing molecule (e.g., streptavidin) 201, 207, which can be the same or different for each surface, to two substrate surfaces 203, 209. The coated substrate surfaces are arranged in opposition to one another at a suitable distance apart. Double-stranded nucleic acids 205, where both ends of one strand comprise a complexing molecule that is complementary to the first complexing molecule (e.g., biotin) which can recognize and bind to the first complexing molecule, are immobilized onto the coated surfaces. Force can be applied to the ends of the immobilized nucleic acids by increasing the distance between the coated surfaces or by lateral translation of one or both surfaces. For example, one or both substrates may be a movable element or comprise a movable element, such as a piezoelectic element. Tension sufficient to cause dsDNA to melt (e.g. greater than about 65 pN at room temperature) can be applied to the nucleic acids, producing anchored strands and freed strands. Both the anchored and the freed strands can be replicated using appropriate primers and polymerase. Preferably, the freed strands can be flushed away and optionally collected so that only the anchored strands will be replicated. The position of the opposed surfaces can be controlled during replication to modulate the amount of tension applied to the anchored template strands. The cycle can be repeated as desired.

In variations of a device for performing the method using opposed coated surfaces 215, 217, one or both surfaces can also be arranged to form an array of individually movable elements 219, each of which may be individually addressed by a control circuit driven by a programmable processor as illustrated in FIG. 2C. Such a control circuit can include a feedback channel that reports force and/or displacement parameters to the processor. Printing or lithography techniques can be used to pattern sites for anchoring molecules on a surface. A device for performing the method can also comprise a channel for introducing reagents to the chamber or channel comprising the coated surfaces and apparatus for delivering (and optionally storing) reagents separately or in combination and for collecting reaction products. A wide variety of suitable methods of anchoring a nucleic acid to a surface are known, including but not limited to covalent bonding, antigen-antibody, and streptavidin-biotin.

Arrangements of fluid flow can be utilized to orient and extend DNA strands between opposed surfaces. For example, as illustrated in FIG. 2B, DNA may be anchored at one end to a surface 213 having passages for fluid flow distributed between the anchoring locations. Flowing fluid though these passages can be used to orient and extend DNA strands more or less uniformly in a desired direction, for example towards an opposed surface 211 or array of movable elements, which may have passages distributed between anchoring surfaces to receive the fluid flow. Thus, a method may comprise anchoring DNA strands to a first surface, flowing fluid through openings in the first surface towards and through openings in a second surface opposed to the first surface, and anchoring DNA strands oriented in the fluid flow to the second surface.

To increase the number of anchored strands with each cycle, activatable primers can be used in replicating the attached strands. "Activatable primers" comprise chemical moieties that can be activated by chemical or physical methods. These "activatable groups" are inert until activated, for example by photoactivation using a laser at an appropriate wavelength. Many different activatable chemical groups are known in the art, which can be converted into or unblock functional complexing groups. In a variation of the method, activatable primers are allowed to anneal to the anchored single-stranded nucleic acids. Primer extension and fragment replication is performed. The resulting double-stranded nucleic acids are denatured through the application of tension to the template strand. The free copy strands will then comprise the activatable groups of the primers. Activation allows the copy strands to become immobilized on the opposing coating surfaces. This cycle can be repeated until a desired degree of amplification is obtained. When desired, anchored nucleic acids can be released, for example by the use of a restriction enzyme that recognizes a sequence near an anchored end of the nucleic acid or that has been introduced into the end of the copied nucleic acid by the primers.

Figure 3A:
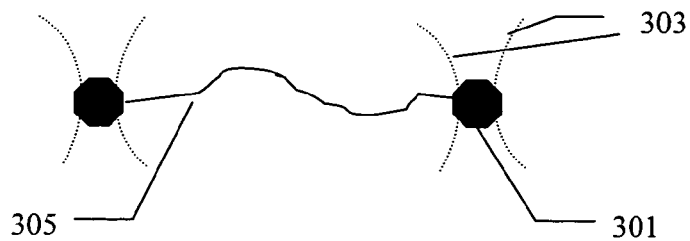
FIGS. 3A and 3B illustrate methods of and arrangements of elements of a reaction chamber for applying tension to a DNA strand using optical or magnetic traps.
Figure 3B:
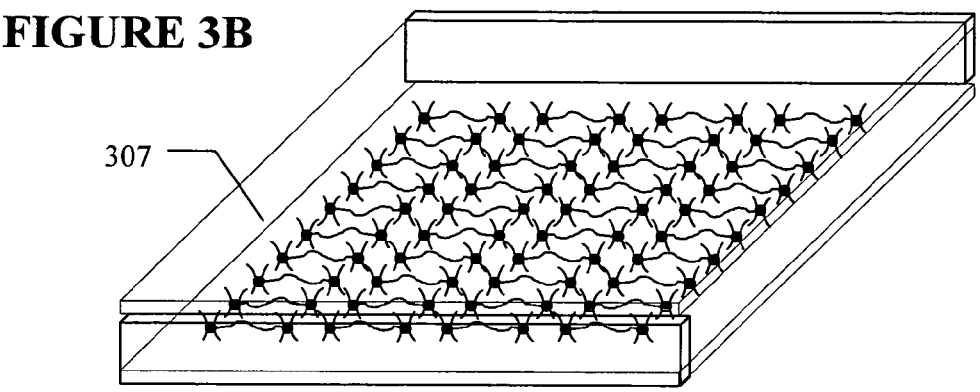

Using Optical or Magnetic Traps:

Another way to directly apply tension to DNA can utilize optical or magnetic tweezers or other traps to manipulate particles to which the DNA is anchored. An optical tweezers traps particles with forces generated by optical intensity gradients. Dielectric particles polarized by the light's electric field are drawn up the gradients to the brightest point. Reflecting, absorbing and low-dielectric particles, by contrast, are driven by radiation pressure to the darkest point. Optically generated forces strong enough to form a three-dimensional trap can be obtained by bringing a laser beam with an appropriately shaped wavefront to a tight focus with a high numerical aperture lens. FIG. 3A illustrates a DNA strand extended between beads 301 tapped at the focus of a laser beam 303. It is possible to manipulate large numbers of particles using an array 307 of optical tweezers as illustrated in FIG. 3B. Commercially available optical tweezers arrays include those produced by Arryx, Inc. Another implementation of an array of optical tweezers, see E. R. Dufresne and D. G. Grier, Rev. Sci. Instr. 69:1974 (1998); and, U.S. Pat. No. 6,055,106 (2000). An optical tweezers array can comprise about $10^3$, $10^4$, $10^5$, $10^6$, or more pairs of optical or magnetic tweezers.

Amplification using optical or magnetic tweezers can generally be performed as follows: A nucleic acid is anchored to appropriate particles at each end in a fluid medium. The particles may be adapted to be manipulated using optical or magnetic traps. Tension sufficient to denature a dsDNA, for example greater than about 65 pN, is applied to the oligonucleotide through the application of force (e.g., optical or magnetic) to the particles, resulting in the denaturation of the nucleic acid. The tension can be reduced in the presence of primers to allow the primers and nucleic acid to anneal. Polymerization by DNA polymerase can be initiated by further relaxing the tension. To repeat the cycle, tension can be increased such that the resulting double-stranded nucleic acids are denatured. In a variation, a nucleic acid can be anchored at one end to a bead that is trapped in a fluid flow, for example by a magnetic field. Fluid flow rate can be used to control tension on the nucleic acid.

It is possible to begin from a single target molecule and sequentially populate an array with copy strands. Copy strands can be anchored to new beads using activatable primers. New beads can be brought into proximity with the copied strands. Alternatively, beads having pre-immobilized primers can be brought into proximity with the copied strands in conjunction with the denaturation step. Manipulation of the beads in this fashion optionally may be automatically controlled by a programmable processor.

Nano-PCR™ Using Hydrodynamic Stress

Nano-PCR™ methods can be performed utilizing the application of tension to DNA by hydrodynamic stress in controlled fluid flow. Methods using this approach can be performed in a microfluidic device, which can be a benchtop device or alternatively can be reduced to a portable size such as may be incorporated in a handheld device. Nano-PCR™ methods utilizing the application of tension to DNA by hydrodynamic stress in controlled fluid flow can be performed using any arrangement that provides for a controlled rate of fluid flow.

Using anchored DNA polymerase: A method of performing a Nano-PCR™ method using polymerase anchored to a surface in a device can comprise the following steps. Polymerase is immobilized on a surface that is arranged such that fluid can be flowed over the surface at a controlled rate. For example, a surface in a channel or chamber that has been coated with a first complexing moiety can be used to immobilize a DNA polymerase that has been modified to comprise a second complexing moiety. Exemplary complexing moieties include antigen-antibody, histidine to Ni-NTA, or biotin-streptavidin pairs. Target dsDNA is denatured in the presence of primers, for example dsDNA and primers can be subjected to a flow rate such that a force sufficient to cause dsDNA to melt (e.g. greater than about 65 pN) is applied to the dsDNA. Polymerase/nucleotide/primer complexes can be allowed to form by reducing the flow rate. Primer extension and fragment replication can be promoted through a further reduction of flow rate. Double-stranded nucleic acid products comprising template and copy strands can be denatured through the application of an increased flow rate, and the cycle can be repeated until a desired degree of amplification is obtained. In such a method, polymerase may be immobilized in a microchannel, for example a microchannel in a microfluidic "lab on a chip" type device.

In variations of a device for performing the method using polymerase anchored on one or more coated surfaces, such a device can also comprise a channel for introducing reagents to a reaction chamber or channel comprising the coated surfaces and apparatus for delivering and optionally storing reagents separately or in combination and for collecting reaction products.

Printing or lithography techniques known in the art can be used to pattern sites for anchoring molecules. Such a device will comprise an apparatus for creating and controlling fluid flow in the reaction chamber or channel. Any suitable method for creating and controlling fluid flow can be used including electrodynamic methods, pumps and syringe apparatuses. Reagent solutions optionally can be recycled through the reaction chamber.

Figure 4:
FIG. 4 is an illustration of an exemplary method of and arrangement of elements of a reaction chamber for applying tension to a DNA strand bound to a polymerase fixed to a substrate in a fluid flow.
Figure 4:
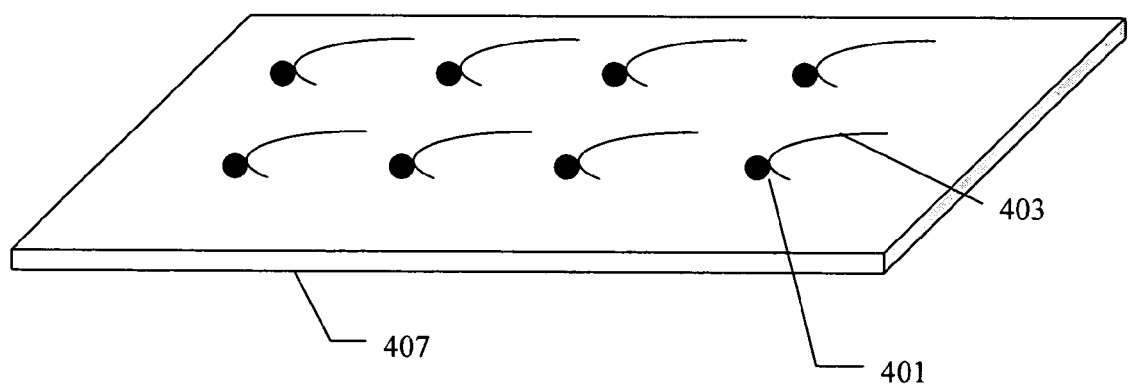

FIG. 4 illustrates an approach in which polymerase 401 is anchored to a substrate 407, for example by streptavidin binding and the like. DNA strands 403 are permitted to bind to the anchored polymerase. Controlled fluid flow 409 passed over the substrate 407 causes application of stretching force on the DNA strands in the form of hydrodynamic stress.

Nano-PCR can be carried out using such an application of force according to the general scheme illustrated in FIG. 1 as described above.

Using anchored DNA strands in a controlled fluid flow: Another way to apply tension to nucleic acids involves immobilized nucleic acids in a controlled fluid flow. The process can generally be performed as follows: Nucleic acids comprising, at one end, a first complexing moiety that recognizes and can bind to a second complexing moiety coated on a surface, are allowed to become immobilized on the coated surface. Fluid is flowed over the surface such that a force sufficient to cause dsDNA to melt (e.g. greater than about 65 pN) is applied to anchored double-stranded nucleic acids, which results in strand separation. DNA polymerase and primers, optionally primers comprising activatable groups, are flushed over the surface at a reduced flow rate. A reduced or stopped flow rate allows formation of polymerase/oligonucleotide/primer complexes. Primer extension and fragment replication can be promoted in the presence of NTPs through a further reduction or stoppage of flow rate. After replication, the flow rate can be increased, subjecting the resulting dsDNA to tension such that the dsDNA is denatured. If activatable primers are used, the extended primers can be activated. These activated, extended primers can be allowed to bind to the coated surface, and the cycle can repeated until a desired degree of amplification is obtained. In such a method, polymerase may be immobilized on a surface in a microchannel, for example a microchannel in a microfluidic "lab on a chip" type device.

Figure 5A:
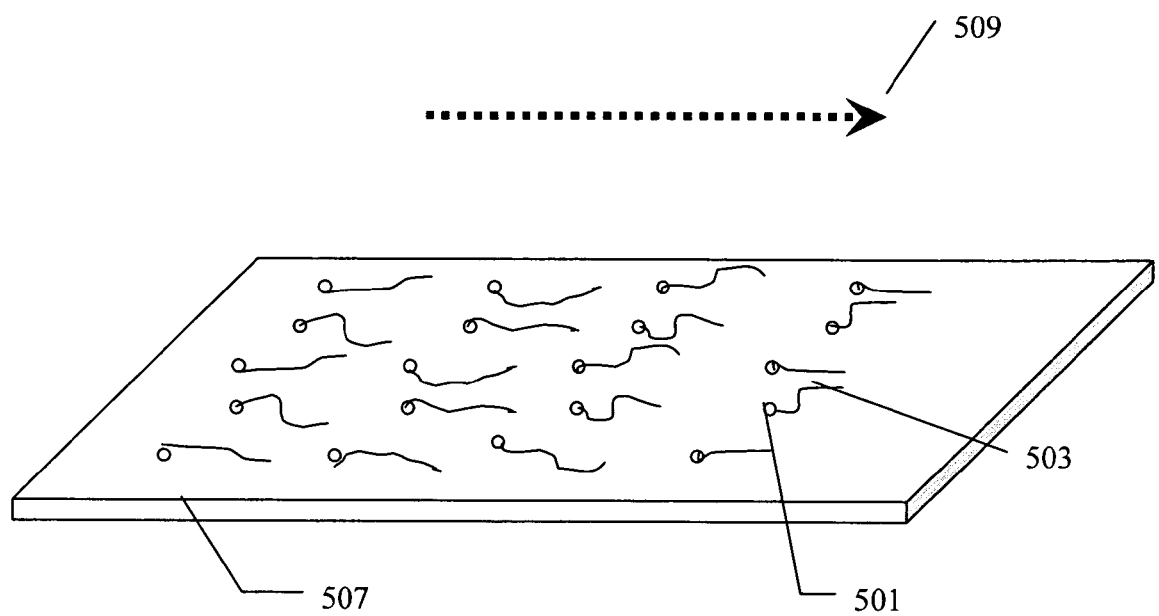
FIGS. 5A and 5B illustrate exemplary methods of and arrangements of elements of a reaction chamber for applying tension to a DNA strand anchored at one end in a fluid flow.
Figure 5B:
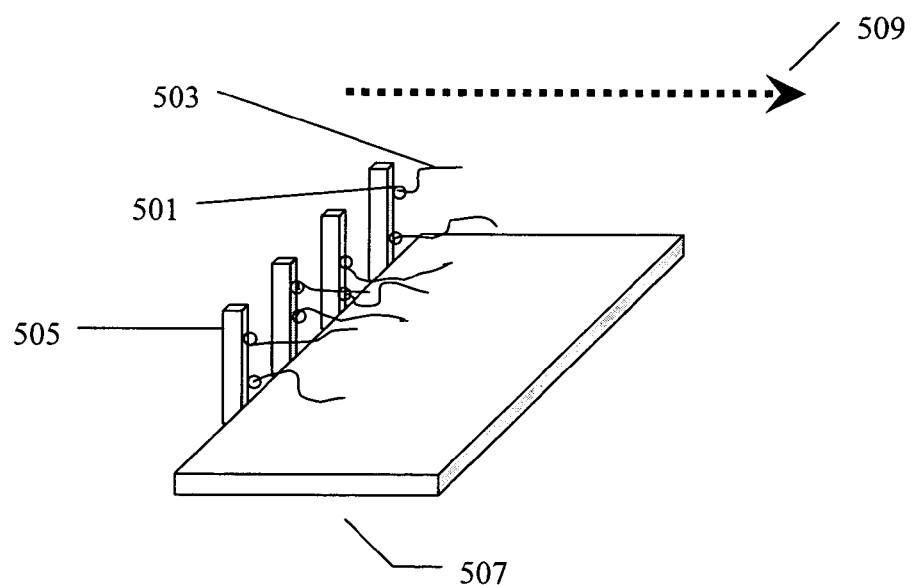

FIG. 5 illustrates the stretching of DNA in a fluid flow by hydrodynamic stress where DNA strands 503 are anchored to a substrate 507 through anchoring molecules 501. Fluid flowing in direction 509 extends and stretches the DNA in a controlled manner as a function of the fluid flow velocity. FIG. 5B illustrates a variation in which DNA strands 503 are anchored by binding molecules 501 to a plurality of substrate structures 505 such that fluid can flow between the structures at a controlled rate. It will be appreciated that there are a large number of other variations that can be used to achieve a similar result.

In variations of a device for performing the method using nucleic acid anchored on one or more coated surfaces, such a device can also comprise a channel for introducing reagents to a reaction chamber or channel comprising the coated surfaces and apparatus for delivering and optionally storing reagents separately or in combination and for collecting reaction products. Printing or lithography techniques known in the art can be used to pattern sites for anchoring molecules. Such a device can comprise an apparatus for creating and controlling fluid flow in the reaction chamber or channel. Any suitable method for creating and controlling fluid flow can be used. For example flow can be provided by means of a pump or can be electrostatically driven. Reagent solutions can optionally be recycled through the reaction chamber.

Stretching DNA in a velocity gradient and using hydrodynamic focusing: An alternative approach to applying tension using fluid flow can be used in combination with the above methods, or may form the basis of a distinct method. DNA can be stretched in a fluid that has a velocity gradient. Various exemplary arrangements for hydrodynamic focusing and counter propagating elongational flows are illustrated in FIGS. 6A-6C.

For example, Wong et al. reviewed the basis of several such techniques and described a method of hydrodynamic focusing (Wong et al., "Deformation of DNA molecules by hydrodynamic focusing." J. Fluid Mech. 497:55-65, 2003). In hydrodynamic focusing, illustrated by FIG. 6A, two streams of buffer 607 flowing at a relatively high rate converge in a microchannel 605 with a center stream that is introduced at a low flow rate. The converging streams accelerate the center stream without substantially mixing. The result is a region of flow having a strong velocity gradient in the flow direction. DNA 601 in this gradient is stretched to an extended state. By increasing the flow rates of the converging streams even more, it will be possible to denature dsDNA such that ssDNA emerges from the microchannel. This permits delivering ssDNA to a reaction chamber, for example where polymerase has been anchored.

Stagnation flow can be used to trap and apply tension to nucleic acids without the need for any anchoring. Perkins et al. described elongation of DNA in a planar elongation flow apparatus ("Single Polymer Dynamics in an Elongation Flow" Science, 276:2016-21, 1997). In Perkins' apparatus, fluid is flowed 623 from opposing directions into a T-shaped junction 625 such as illustrated in FIG. 6C. At the center of the junction, a stagnation point 629 is established. Outside of this point, a fluid velocity gradient is established. DNA 601 can become trapped at the stagnation point, being pulled equally in opposite directions by the velocity gradient. Alternative arrangements such as channel 615 illustrated in FIG. 6B can include offset jets 617 of fluid entering a channel 615, or flowing buffer in opposing directions across a slot in which nucleic acid resides.

Nano-PCR™ Methods Using Cycling of Applied Electric Fields

It is possible to apply force to DNA strands in Nano-PCR™ methods through the use of electric and magnetic fields. There are a variety of ways that this can be accomplished. For example, electric fields can be used to indirectly apply force to DNA by driving fluid flow in a microfluidic device. As described above, fluid flow can be used to apply hydrodynamic stress to DNA, for example, DNA anchored to a surface and/or to a particle, or bound to a DNA polymerase that is anchored to a surface. Electrophoretic forces can also apply force directly to DNA strands.

Electric fields may also be used to manipulate DNA strands bound to conductive particles. Accordingly, Nano-PCR™ methods can be performed where denaturation, annealing, and/or primer extension steps are controlled by a non-thermally-driven process wherein one or both ends of a DNA strand is bound to a conductive particle, e.g. gold nanoparticles or the like, which can be manipulated by electric fields to apply tension to the DNA strand. Where one end of a DNA molecule is attached to a conductive particle, the other end can be anchored to a surface in a reaction chamber in a device. Such methods may utilize activatable primers as described herein to anchor DNA strands produced in each cycle.

Exemplary Applications of Nano-PCR™ Methods

Nano-PCR™ methods can be employed in kits and systems for pathogen and bioweapon detection. Examples of such pathogens include, without limitation: Adeno-associated Virus (AAV), Adenovirus, Cytomegalovirus (CMV), Epstein-Barr Virus, Enterovirus, Hepatitis A Virus (HAV), Hepatitis B Virus (HBV), Hepatitis C Virus (HCV), Human Herpes Virus Type 6 (HHV-6), Human Immunodeficiency Virus Type 1 (HIV-1), Human Immunodeficiency Virus Type 2 (HIV-2), Herpes Simplex Virus Type 1 and Type 2 (HSV-1 and HSV-2), Human T-Cell Lymphotropic Virus Type I and Type II (HTLV-I and HTLV-II), *Mycobacterium tuberculosis, Mycoplasma*, Parvovirus B-19, Respiratory Synctitial Virus (RSV) and Porcine Endogenous Retrovirus (PERV). Nano-PCR™ methods can be used for detection of any pathogen in any environment because of the enhancements in sensitivity, accuracy and robustness these methods can provide.

The detection and identification of a particular pathogen using conventional PCR-based diagnostics generally requires that the pathogenic organism or its polynucleotide be present in a biological fluid (e.g. blood, saliva, etc.) at a certain threshold concentration. The lower detection limit of *Mycobacterium tuberculosis*, for example, has been reported as $7.5 \times 10^3$ organisms/ml. HCV RNA is detectable in a range from 100 to 1000 RNA molecules/ml. Shim has reported that the polymerase chain reaction detects around 87.5 percent of proven *Mycobacterium tuberculosis*-containing nodules. That corresponds to a false-negative rate for detection of 12.5 percent. In preferred embodiments Nano-PCR™ methods can be used to detect pathogens such as the above with false-negative rates typically less than 12.5 percent, 10 percent, 5 percent, 2.5 percent, 1 percent, 0.5 percent, 0.25 percent, or 0.1 percent.

Furthermore, Nano-PCR™, can be performed such that it is not limited to about 30-35 cycles of amplification as conventional PCR generally is. This is because of degradation of polymerase after repeated cycles of heating above the DNA melting temperature. In contrast, Nano-PCR™ methods can optionally comprise 40, 50, 60, 70, 100, or more cycles. As Nano-PCR™ can be performed in an isothermal manner, or using low amplitude temperature modulation, Nano-PCR™ can be repeated for many cycles, limited only by the lifetime of the enzyme (e.g. at room temperature).

Thus Nano-PCR™ methods can be used to amplify amounts of starting material (either organisms or their DNA or RNA) that are substantially less than amounts required by conventional PCR. Nano-PCR™ methods can be used to detect and reliably amplify as little as a single molecule of DNA or RNA, dramatically decreasing the false-negative rate and providing increased sensitivity of as much as 100%. For pathogens such as those exemplified above, organisms or polynucleotides can be detected at concentrations lower than 1000 organisms or polynucleotides/ml, 100 organisms or polynucleotides/ml, 50 organisms or polynucleotides/ml, 25 organisms or polynucleotides/ml, 10 organisms or polynucleotides/ml, 5 organisms or polynucleotides/ml, or even as little as 1 organism or polynucleotide/ml.

An exemplary variation of the method can be used for detecting the presence or absence of at least one specific DNA sequence or distinguishing between two different DNA sequences in a sample. In such a variation, target DNA can be amplified as described above. The method can further comprise: contacting the amplified DNA with a probe or probes (e.g., an oligonucleotide complementary to the sequence to be detected that also comprises a detectable moiety, such as a fluorescent label); and, detecting whether the specific DNA sequence is in the sample by observing the presence or absence of the probe bound to the amplified DNA, or distinguishing between two different sequences by detecting which of a plurality of probes is bound to the amplified DNA.

Another variation of the method can be used for amplification and/or detection of a sequence encoded on RNA. The target sequence can be encoded on an isolated RNA or on RNA in a mixture of nucleic acids. The method can comprise: isolating RNA from a sample (e.g., tissue or fluid); performing reverse transcription thereby obtaining a corresponding cDNA; and, amplifying the target sequence as described above. Such methods can further comprise detecting the presence of a specific sequence in the sample as described above.

Another variation of the method can be used for sequencing a DNA. Such a method can comprise optionally amplifying the DNA as described above and sequencing the DNA. Sequencing the DNA can comprise (a) providing a sample of dsDNA containing a target sequence, the sample being divided into four parallel reactions, a primer complementary to the 3' end of the target sequence; at least four different nucleoside triphosphates (i.e. ATP, CTP, GTP, TTP); providing a different dideoxy nucleoside triphosphate (ddNTP) selected from among ddATP, ddCTP, ddGTP, and ddTTP optionally labeled with a detectable chemical moiety such as a fluorescent moiety, and a DNA polymerase in each parallel reaction; (b) denaturing the dsDNA into ssDNA template strands using a non-thermally-driven process, for example by the application of tension sufficient to cause dsDNA to melt (e.g. greater than about 65 pN) to the dsDNA; (c) controlling the non-thermally-driven process to promote hybridization of primers to complementary template strands, for example, where tension was used to denature the dsDNA, by reducing the tension applied to the ssDNA; (d) permitting the DNAp to extend the primers to form dsDNA; (e) optionally repeating steps (b-d) until a desired amount of DNA sequence amplification is obtained, and determining the sequence by detecting the length of each nucleotide produced in the reaction or by detecting the base specific fluorescent moiety or some other base-specific signal as in various single molecule sequencing schemes.

Nano-PCR™ Devices

There are many different device types and configurations one can use to perform non-thermally-driven polymerase chain reactions as described herein. One such device is a microfluidic device, where the flow rate within microfluidic channels on the device is controllable and variable. In preferred embodiments, a device will have a reaction chamber, which can be a channel, an arrangement of channels, or an enclosed space. The reaction chamber will generally comprise a means of retaining nucleic acids and a means of applying stress or tension to the nucleic acids retained therein. Thus, arrangements designed to carry out any of the methods described herein can be envisioned comprising a combination of channels and enclosed spaces having disposed therein particles capable of binding nucleic acids or complexing molecules capable of securing their complementary complexing molecules, surfaces having complexing molecules, movable elements, channels for directing fluid flow and generating a fluid velocity gradient, pumps, valves, membranes, and the like. The chamber can comprise an optically transparent window, for example, if optical micromanipulators are to be used. The devices can be manufactured as microfluidic devices which may be incorporated into handheld units. If desired, Nano-PCR™ can be performed in solution volumes of less than about a microliter, for example about 50-1000 nL, preferably about 100-500 nL.

Figure 7A:
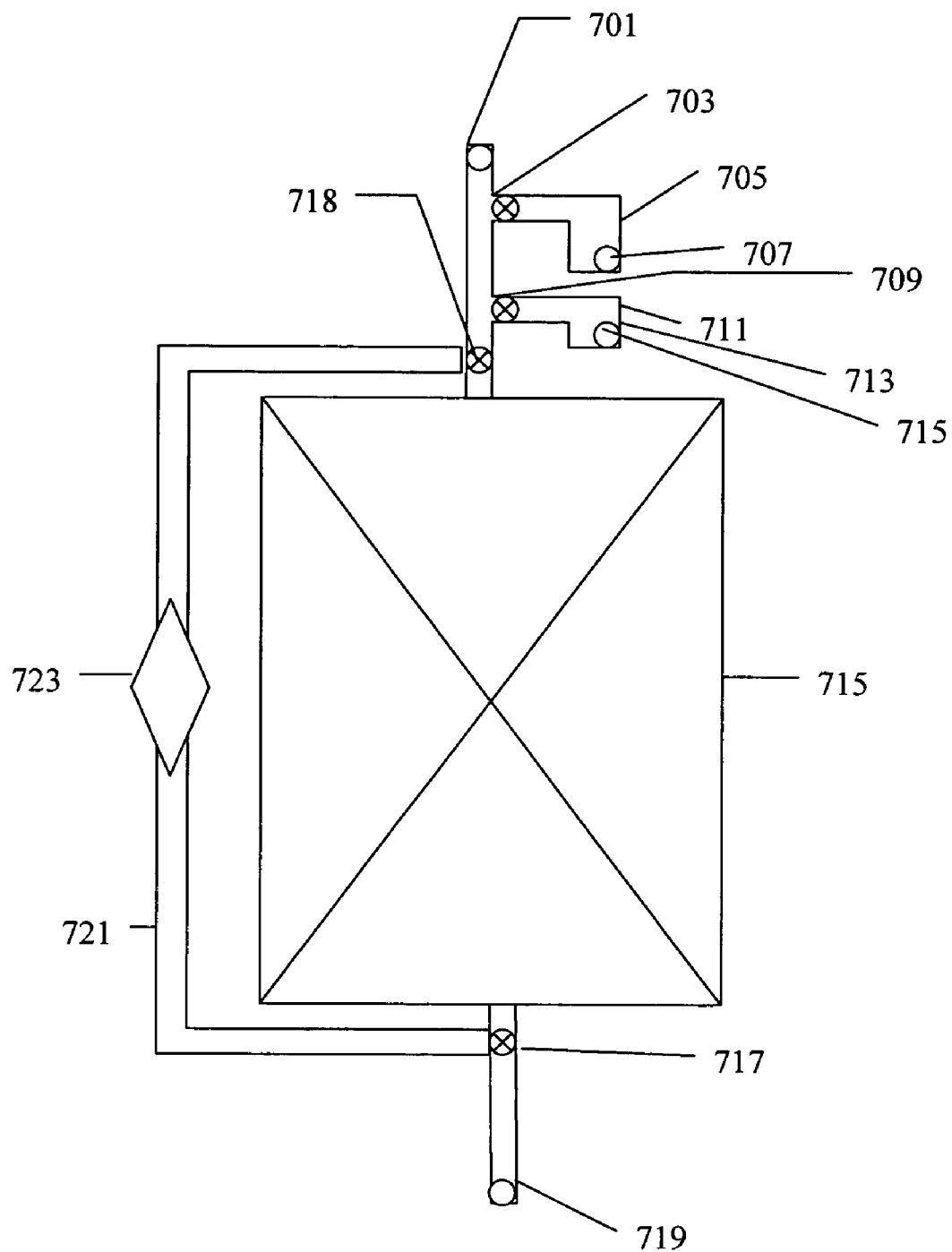
FIGS. 7A and 7B illustrate schematics of exemplary devices for performing a PCR method that does not rely on temperature cycling or thermal denaturation.
Figure 7B:
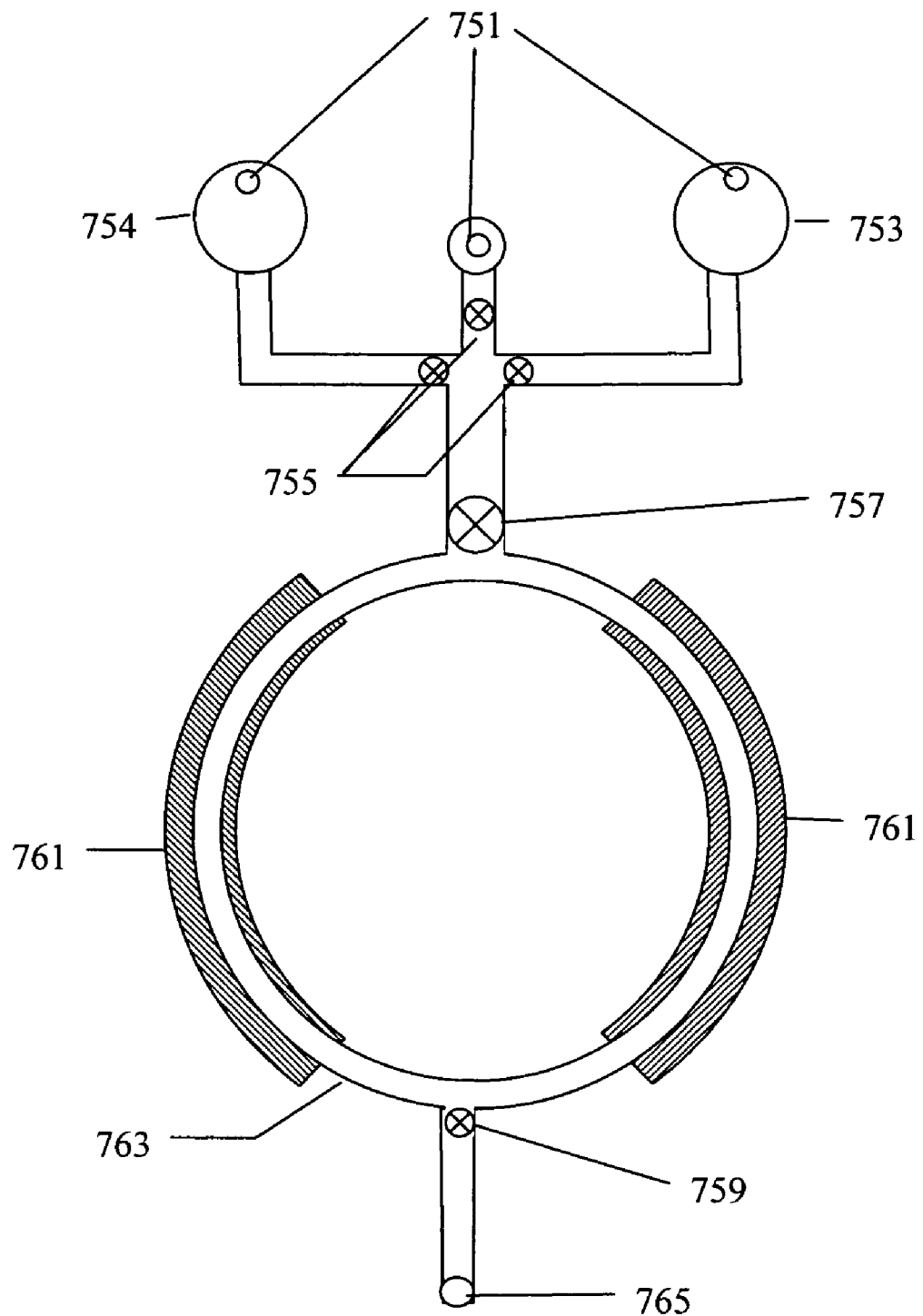

As an example, FIG. 7A illustrates a possible configuration of a device in which reagents can be introduced through inlets 701, 707 and 715. One or more storage chambers 705, 711 can be provided to contain prepared buffers, dideoxy nucleotide triphosphates, polymerase, and the like. Valves 703, 709, 717 and 718 may comprise one or more fluid gates arranged to control fluid flow at junctions between channels. Reaction chamber 715 may be arranged to permit controlled application of tension to nucleic acid molecules therein, for example as illustrated in FIGS. 2-6. A channel 721 and pump 723 are optionally provided to permit recycling and controlled flow of regents through chamber 715. Pump 723 may operate by any appropriate mechanism recognized in the art, for example peristaltic pumping, pumping by use of one or more bellows or pistons, by electromotive force, and variations or combinations of such devices and the like. Where recycling is not desired, flow may be controlled within chamber 715 or externally, for example by syringes attached at inlet and/or outlets 701 and 719. An example of a microfluidic device utilizing a circular, or roughly circular, channel configuration is illustrated by FIG. 7B. Inlets 751 permit introduction of reagents either directly to a channel feeding reaction channel 763 or into one or more storage chambers 753, 754 for later use. Valves 755, 757, and 759 control flow into and out of the reaction channel. Pumps 761 may operate to control fluid velocity in channel 763 by peristaltic action, for example by deflection of one or more valve gates into channel 763 in a sequentially controlled manner, electromotive force, or any other means recognized in the microfluidics art. For example, a device may be constructed using valves and a peristaltic pumping arrangement that comprise structures constructed of elastomeric material that can be deflected into the channels of the device in a controlled sequence to control flow, such as described in published PCT application WO/02081729.

The operation of the device illustrated in FIG. 7B can be further understood through a description of its operation during a non-thermally-driven polymerase chain reaction. In the specific instance of nucleic acid amplification reactions, a sample containing or potentially containing a target nucleic acid is introduced into loop 763 through an inlet 751. In some examples, one or more walls of the loop 763 have been prepared for anchoring polymerase or nucleotides as illustrated in FIGS. 4-5. Alternatively, the loop may be arranged to create fluid velocity gradients, counter propagating fluid flow, and the like by utilizing additional inlets or rotating surfaces such as illustrated in FIG. 6. Other reagents necessary to conduct the amplification reaction are similarly introduced through the inlets. Typical reagents include a primer or primers (e.g., forward and reverse primers) that specifically hybridize to the target nucleic acid, the four deoxynucleoside triphosphates (i.e., dATP, dTTP, dGTP and dCTP), a polymerase, a buffer and various cofactors required by the polymerase (e.g., metal ion).

Following introduction of the sample and necessary amplification reagents into loop 763, the resulting solution is circulated under the action of pumps 761. By varying the rate of pump action, one can control the solution circulation/flow rate. A flow rate resulting in application of about 65 pN of force to the target nucleic acid is established, which denatures it. The flow rate is decreased such that the force applied to the target nucleic acid is in a range from about 30 pN to 60 pN. This allows formation of polymerase/nucleic acid/primer complexes. Primer extension is initiated by further reducing the flow rate to a value corresponding to less than 30 pN of applied force. Upon completion of primer extension, the flow rate is again increased to denature the resulting double-stranded nucleic acid. The recited steps are repeated until a desired quantity of target nucleic acid is obtained. One can access the amplified target nucleic acid by flushing solution through outlet 765 by opening valve 759.

An apparatus for conducting Nano-PCR™ methods can comprise a programmable control device that can individually address and control elements of the reaction device and may also include sensors and feedback circuits so that the control device can monitor, analyze, and if desired can adjust reaction parameters, such as applied stress and template extension.

EXAMPLES

Example 1

Method and Device Using Opposing Coated Surfaces

A pair of streptavidin-coated surfaces are prepared according to standard methods. (Sabanayagam, Smith, and Cantor. "Oligonucleotide immobilization on micropatterned streptavidin surfaces." Nucleic Acids Res. 2000, Vol. 28, No. 8 pp. i-iv) Biotinylated dsDNA (biotinylation at both ends of one strand) is added to the surfaces, which immobilizes the dsDNA between the surfaces. Jeffrey M. Rothenberg and Meir Wilchek. p-Diazobenzoyl-biocytin: a new biotinylating reagent for DNA Nucleic Acids Research Volume 16 Number 14 1988) By adjusting the concentration of the template that is applied to the surface, the surface density of the DNA molecules can be controlled. At room temperature, greater than about 65 pN of tension is applied to the dsDNA by increasing the distance between the coated surfaces. This denatures the dsDNA, leaving only target ssDNA for amplification. The bound DNA is contacted with primers comprising caged biotin groups, while the distance between the surfaces is reduced so that between 30 pN and 60 pN is applied to the immobilized ssDNA. The primers are allowed to anneal to the target DNA, and DNA polymerase and nucleotides are added to the resulting complex. Primer extension is initiated by further reducing the applied tension to <30 pN. Once primer extension is complete, a force >65 pN is applied to the resulting duplex by increasing the distance between the surfaces. This application of force denatures replica nucleotide strand from its template. The replica strands containing caged biotin moieties are photoactivated and allowed to bind to the streptavidin-coated, opposing surfaces. The above-recited steps are repeated until a desired degree of amplification is obtained for the target nucleotide.

Caged biotin reagents can be purchased from commercial vendors such as Molecular Probes or Pierce. For example, a derivative of biotin with a photoactivatable nitrobenzyl group (MeNPOC-biotin) exists in a form well-suited for easy linkage to biomolecules and surfaces. (Pirrung M C, Huang C Y. A general method for the spatially defined immobilization of biomolecules on glass surfaces using "caged" biotin. Bioconjug Chem. 1996 May-June; 7(3):317-21)

Example 2

Method and Device Using Immobilized Polymerase

A streptavidin-coated microchannel surface is prepared according to standard methods. Sabanayagam, Smith, and Cantor. "Oligonucleotide immobilization on micropatterned streptavidin surfaces." Nucleic Acids Res. 2000, Vol. 28, No. 8 pp. i-iv) Biotinylated DNA polymerase is flushed into the microchannel and incubated to allow surface saturation. Commercial kits for the biotinylation of enzymes are available, for example, from Pierce Labs. Unbound enzyme is flushed out of the microchannel and target nucleotide (e.g., ssDNA, RNA) and primers are flushed in at a chamber flow rate that applies >60 pN of force on the nucleotide. The polymerase/nucleotide/primer complex is allowed to form by reducing the flow rate such that a force between 30 pN and 60 pN is applied to the nucleotide. Primer extension is allowed to occur by further reducing the chamber flow rate to <30 pN. Once primer extension is complete, a force >65 pN is applied to the resulting duplex by increasing flow rate. This application of force denatures replica nucleotide strand from its template. The denatured strands are allowed to cycle through the microfluidic chamber until polymerase binding occurs, and the above-recited steps are repeated until a desired degree of amplification is obtained for the target nucleotide.

Example 3

Method and Device Using DNA Immobilization

A streptavidin-coated microchannel surface is prepared according to standard methods. (Sabanayagam, Smith, and Cantor. "Oligonucleotide immobilization on micropatterned streptavidin surfaces." Nucleic Acids Res. 2000, Vol. 28, No. 8 pp. i-iv. Biotinylated dsDNA (biotinylation at one end of one strand) is flushed into the microchannel and incubated to allow surface binding. (Jeffrey M. Rothenberg and Meir Wilchek. p-Diazobenzoyl-biocytin: a new biotinylating reagent for DNA Nucleic Acids Research Volume 16 Number 14 1988) A chamber flow rate that applies a force >65 pN to the bound dsDNA is established. This denatures the dsDNA, leaving only target ssDNA for amplification. DNA polymerase, nucleotides, and caged biotinylated primers are flushed into the microchannel. Caged biotin reagents can be purchased from commercial vendors such as Molecular Probes or Pierce. For example, a derivative of biotin with a photoactivatable nitrobenzyl group (MeNPOC-biotin) exists in a form well-suited for easy linkage to biomolecules and surfaces. (Pirrung M C, Huang C Y. A general method for the spatially defined immobilization of biomolecules on glass surfaces using "caged" biotin. Bioconjug Chem. 1996 May-June; 7(3):317-21). The chamber flow rate is decreased such that between 30 pN and 60 pN is applied to the bound ss DNA. The primers are allowed to anneal to the target DNA, and the resulting compounds are allowed to complex to DNA polymerase. Primer extension is allowed to occur by further reducing the chamber flow rate to <30 pN. Once primer extension is complete, a force >65 pN is applied to the resulting duplex by increasing flow rate. This application of force denatures replica nucleotide strand from its template. The replica strands containing caged biotin moieties are photoactivated and allowed to bind to the streptavidin-coated microchannel surface. The above-recited steps are repeated until a desired degree of amplification is obtained for the target nucleotide.

Example 4

Method and Device Using Optical Tweezers

A double-stranded DNA complex is immobilized between polystyrene beads in an appropriate medium at ambient temperature. ("Overstretching B-DNA: the Elastic Response of Individual Double Stranded and Single Stranded DNA Molecules" by Steven B. Smith, Yujia Cui, and Carlos Bustamante *Science* (1996) vol. 271, pp. 795-799) A stretching force of approximately 65 pN is applied to the DNA through the use of optical tweezers. (Rouzina, I., and V. A. Bloomfield. 2001b. Force-induced melting of the DNA double helix 2. Effect of solution conditions. *Biophys. J.* 80:894-900) The force results in DNA denaturation. Primers are added to the medium, and the stretching force is reduced to less than 60 pN. This allows the primers to anneal to the denatured, single-stranded DNA. DNA polymerase and nucleotides are added to the medium, and highly accurate replication is initiated by reducing the stretching force to between 0 and 30 pN. After replication is complete, a stretching force of approximately 65 pN is applied to each of the double-stranded DNA complexes, resulting in the release of single-stranded DNA molecules. This can be scaled up by using an array of manipulators. For example, an array such as the optical trap arrays made by Arryx, Inc. can be used.

While the invention has been described in detail with reference to particular embodiments thereof, it will be apparent to one skilled in the art that various changes can be made, and equivalents employed, without departing from the scope of the invention.

What is claimed is:

1. A method for amplifying a nucleic acid, comprising:
   (a) contacting one or more template strands of single-stranded nucleic acid with one or more oligonucleotide primers complementary to a portion of the one or more template strands;
   (b) annealing at least one primer of the one or more primers to the portion of the one or more template strands to which the primer is complementary;
   (c) contacting the one or more template strands with a nucleic acid polymerase and at least four different nucleoside triphosphates;
   (d) extending the at least one annealed primer by the nucleic acid polymerase thereby forming one or more extension products bound to the one or more template strands;
   (e) separating the one or more extension products from the one or more template strands; and
   (f) repeating steps (a), (b), (c), (d) and (e) to amplify the nucleic acid, wherein at least one of the one or more extension products in step (e) is used as template strands in a subsequent cycle of steps (a)-(e),
   wherein, for the last cycle, step (e) is optional, and
   wherein at least one of steps (b) or (d) comprises applying tension that tends to stretch the nucleic acid to the one or more template strands.

2. The method of claim 1, wherein steps (b) and (d) each comprise applying tension to the one or more template strands.

3. The method of claim 1, wherein steps (d) and (e) each comprise applying tension that tends to stretch the nucleic acid to the one or more template strands.

4. The method of claim 3, wherein applying tension in step (e) comprises applying increased amounts of the same type of tension as applied in step (d).

5. The method of claim 1, wherein steps (b) and (e) each comprise applying tension that tends to stretch the nucleic acid to the one or more template strands.

6. The method of claim 1, wherein steps (b), (d) and (e) each comprise applying tension that tends to stretch the nucleic acid to the one or more template strands.

7. The method of claim 1, wherein applying tension to the one or more template strands comprises applying mechanical tension, hydrodynamic stress, or electrical field energy to the one or more template strands.

8. The method of claim 1, wherein applying tension to the one or more template strands comprises applying a controlled amount of mechanical tension to the one or more template strands.

9. The method of claim 8, wherein applying a controlled amount of mechanical tension to the one or more template strands comprises moving a surface to which the one or more template strands are attached.

10. The method of claim 1, wherein applying tension to the one or more template strands comprises controlling hydrodynamic tension caused by fluid flow on the one or more template strands.

11. The method of claim 10, wherein the one or more template strands are anchored to a surface exposed to a fluid flow, the one or more template strands are bound to a DNA polymerase anchored to a surface exposed to a fluid flow, or the one or more template strands are retained and extended by counter-propagating fluid flows.

12. The method of claim 1, wherein applying tension to the one or more template strands comprises applying force to one or more particles connected to one or both ends of at least one strand of the one or more template strands.

13. The method of claim 1, wherein step (b) comprises applying tension to the one or more template strands within the range of about 0 to about 65 pN.

14. The method of claim 1, wherein step (b) comprises applying tension to the one or more template strands within the range of about 10 to about 65 pN.

15. The method of claim 1, wherein step (d) comprises applying tension to the one or more template strands from greater than 0 pN to about 45 pN.

16. The method of claim 1, wherein step (d) comprises applying tension to the one or more template strands and increasing the tension applied at a time corresponding to a period during which a difficult sequence on the nucleic acid is replicated.

17. The method of claim 16, wherein the nucleic acid comprises one or more segments of several residues which have a GC content greater than 50 percent and the nucleic acid is amplified at greater than 90 percent efficiency.

18. The method of claim 16, wherein the nucleic acid comprises one or more segments of several residues which have a GC content greater than 60 percent.

19. The method of claim 16, wherein the nucleic acid comprises one or more segments comprising a repeating unit of 8 or more base pairs and the nucleic acid is amplified at greater than 90 percent efficiency.

20. The method of claim 1, wherein steps (a), (b), (c), (d) and (e) are conducted at below about 65° C.

21. The method of claim 1, wherein the steps (a), (b), (c), (d) and (e) are repeated at least about 50 times.

22. The method of claim 21, wherein a template strand of greater than about 1000 bases is amplified.

23. The method of claim 22, wherein the method is completed in about 1 hour or less.

24. The method of claim 1, wherein the nucleic acid is amplified in a solution with a pH of 4-7 or 8-10.

25. The method of claim 1, carried out in a reaction chamber having a volume of less than about a microliter.

26. The method of claim 1, further comprising prior to the first instance of step (a):
   obtaining a sample of RNA,
   contacting the RNA with a reverse transcriptase in the presence of a composition sufficient to permit creation of a complementary DNA strand, and
   separating the DNA from the RNA to form the single stranded nucleic acid.

27. The method of claim 1, further comprising prior to the first instance of step (a):
   obtaining a sample of DNA,
   denaturing said DNA,
   binding the denatured DNA to a substrate in a reaction chamber, and
   flushing said reaction chamber to remove contaminants from said sample.

28. The method of claim 1 wherein, in the first instance of step (a), the one or more template strands are obtained from a single molecule of DNA.

29. The method of claim 1 wherein, in at least the first instance of step (a), the one or more template strands are contained in an unpurified sample of material.

30. A method of detecting a pathogen comprising the method of claim 1 and further comprising probing the amplified nucleic acid for the presence of a nucleotide sequence specifically associated with the pathogen.

31. The method of claim 30, wherein the pathogen is selected from the group consisting of Adeno-associated Virus, Adenovirus, Cytomegalovirus, Epstein-Barr Virus, Enterovirus, Hepatitis A Virus, Hepatitis B Virus, Hepatitis C Virus, Human Herpes Virus Type 6, Human Immunodeficiency Virus Type 1, Human Immunodeficiency Virus Type 2, Human T-Cell Lymphotropic Virus Type I, Human T-Cell Lymphotropic Virus Type II, Mycobacterium Tuberculosis, Mycoplasma, Parvovirus B-19, and Porcine Endogenous Retrovirus.

32. The method of claim 30 comprising obtaining a sample containing less than about 1000 organisms or polynucleotides per milliliter from which the template strands for the first cycle of amplification are prepared.

33. A method for amplifying a nucleic acid, comprising:
   (a) contacting one or more template strands of single-stranded nucleic acid with one or more oligonucleotide primers complementary to a portion of the one or more template strands, wherein at least one primer of the one or more primers comprises one or more complexing groups capable of binding one or more molecules bound to a substrate;
   (b) annealing the at least one primer with the one or more complexing groups to the portion of the one or more template strands to which the primer is complementary, thereby binding the one or more template strands to the substrate;
   (c) contacting the one or more template strands with a nucleic acid polymerase and at least four different nucleoside triphosphates;
   (d) extending the one or more primers by the nucleic acid polymerase thereby forming one or more extension products bound to the one or more template strands;
   (e) separating the one or more extension products from the one or more template strands; and
   (f) repeating steps (a), (b), (c), (d) and (e) to amplify the nucleic acid, wherein, in the last cycle, step (e) is optional,
      wherein at least one of the one or more extension products in step (e) is used as template strands in a subsequent cycle of steps (a)-(e), and
      wherein at least one of steps (b), (d), and (e) comprises applying tension that tends to stretch the nucleic acid to the one or more template strands.

34. The method of claim 33, wherein the one or more complexing groups are activatable.

35. The method of claim 33, wherein the one or more complexing groups and the one or more molecules bound to the substrate are biotin and streptavidin, respectively.

36. The method of claim 33, wherein the one or more complexing groups comprise photoactivatable caged biotin.

37. A method for amplifying a nucleic acid, comprising:
   (a) denaturing a double-stranded nucleic acid molecule by applying tension that tends to stretch the nucleic acid to one or both strands of the double-stranded nucleic acid molecule sufficient to cause separation of the double-stranded nucleic acid molecule into two single-stranded nucleic acid molecules, wherein the one or both single-stranded nucleic acid molecules to which the tension is applied becomes a template strand;
   (b) contacting the one or both template strands with one or more oligonucleotide primers complementary to a portion of the template strands, a nucleic acid polymerase and at least four different nucleoside triphosphates;
   (c) reducing the tension applied to the one or both template strands in step a) to permit the one or more primers to anneal to the corresponding portions of the template strands to which the one or more primers are complementary;
   (d) controlling the tension applied to the one or both template strands so as to permit extension of the one or more primers by the nucleic acid polymerase, thereby forming one or more double-stranded nucleic acid molecules in which one or more extension products are bound to the one or more template strands; and
   (e) repeating steps (a), (b), (c), and (d) to amplify the nucleic acid,
      wherein at least one of the one or more double-stranded nucleic acid molecules formed in step (d) in a cycle of steps (a)-(d) is used as the double-stranded nucleic acid molecule in step (a) in a subsequent cycle of steps (a)-(d), so that at least one extension product formed in step (d) is used as a template strand in a subsequent cycle of steps (a)-(d).

38. The method of claim 37, wherein at least one of applying, reducing, and controlling the tension comprises binding the nucleic acid molecules to which the tension is applied to a substrate or one or more particles or both and controlling movement of said substrate or the one or more particles or both.

39. The method of claim 37, wherein at least one of applying, reducing, and controlling the tension comprises binding the nucleic acid molecules to which the tension is applied to one or more particles and controlling movement of said one or more particles by optical or magnetic manipulation.

40. The method of claim 37, wherein at least one of applying, reducing, and controlling the tension comprises modulating fluid flow over the nucleic acid molecules to which the tension is applied.

41. The method of claim 37, wherein at least one of said nucleic acid molecules is bound by a polymerase that is bound to the substrate, and wherein fluid is flowed over the substrate.

42. The method of claim 37, wherein at least one of said nucleic acid molecules is bound to a substrate.

43. The method of claim 37, wherein at least one of said nucleic acid molecules is stretched in a fluid flow velocity gradient.

44. The method of claim 37, wherein at least one of said nucleic acid molecules is stretched by a counter propagating fluid flow.

45. The method of claim 37, wherein step (d) comprises increasing the tension at a time corresponding to a period during which a difficult sequence on the one or more template strands is replicated.

46. A method comprising:
   (a) providing a sample of double-stranded DNA (dsDNA) containing a target sequence, oligonucleotide primers complimentary to the 3' ends of the target sequence and its complement; at least four different nucleoside triphosphates and a DNA polymerase;
   (b) denaturing the dsDNA into single-stranded DNA (ssDNA) molecules by applying tension that tends to stretch the nucleic acid to one or both strands of the dsDNA sufficient to cause the dsDNA to melt, wherein the one or both resulting ssDNA molecules becomes a template strand;
   (c) reducing the tension applied to the one or both template strands sufficient to permit hybridization of at least one of the primers to its complementary sequence in the template strands;
   (d) modulating the tension applied to the one or both template strands to a level allowing the DNA polymerase to extend the at least one primer to form an extension product, thereby forming one or more molecules of dsDNA; and
   (e) repeating steps (b) through (d) to amplify the dsDNA provided in step (a), wherein at least one of the one or more molecules of dsDNA formed in step (d) in a cycle of steps (b) through (d) is denatured in step (b) in a subsequent cycle of steps (b) through (d), so that at least one extension product formed in step (d) is used as a template strand in a subsequent cycle of steps (a)-(d).

47. The method of claim 46, wherein the entire process is carried out at ambient temperature.

48. The method of claim 46, wherein the process is carried out at a temperature above about 20° C. and below about 60° C.

49. The method of claim 46, wherein the process is carried out at room temperature and the tension in step b) is above about 65 pN, in step c) the tension is reduced to between about 0 pN to about 60 pN, and in step d) the tension is modulated between about 0 pN to about 45 pN.

50. The method of claim 46, wherein the tension is caused and controlled by electrically, magnetically, or optically manipulating one or more particles attached to the DNA, by moving a surface to which the DNA is attached, by controlling a fluid flow to which the DNA is exposed, or a combination of these methods.

51. A method of performing nucleic acid amplification by a polymerase chain reaction, comprising:
   (a) denaturing a double-stranded nucleic acid to produce single-stranded template strands;
   (b) annealing primers to the template strands; and
   (c) extending the primers by a template-strand-driven polymerase to produce extension products, thereby forming double-stranded nucleic acid molecules; and
   (d) repeating steps (a)-(c) to amplify the double-stranded nucleic acid,
      wherein at least one of the double-stranded nucleic acid molecules produced in step (c) in a cycle of steps (a)-(c) is denatured in step (a) in a subsequent cycle of steps (a)-(c), so that at least one extension product formed in step (c) is used as a template strand in a subsequent cycle of steps (a)-(d), and
      wherein at least one of steps (b) and (c) comprises applying tension that tends to stretch the nucleic acid to the nucleic acid.

52. The method of claim 51, wherein applying tension comprises applying mechanical tension, hydrodynamic stress, or electromagnetic force, or any combination thereof.

53. The method of claim 51, wherein steps (a) though (d) are performed at temperature below 80° C.

54. The method of claim 51, wherein steps (a) though (d) are performed at temperature below 30° C.

55. The method of claim 51, wherein the method is performed at an ambient temperature.

56. The method of claim 51, wherein tension that tends to stretch the nucleic acid applied in step (a) is equal to or greater than 65 pN.

57. The method of claim 51, wherein tension applied in step (b) is equal to or less than 50 pN.

58. The method of claim 51, wherein tension applied in step (b) is from 30 pN to 50 pN, inclusive.

59. The method of claim 51, wherein tension applied in step (c) is equal to or less than 45 pN.

60. The method of claim 51, wherein tension applied in step (b) is from 35 pN to 45 pN, inclusive.

61. The method of claim 51, wherein the single-stranded template strands produced in the first instance of step (a) are produced by denaturing a single molecule of double-stranded nucleic acid.

62. The method of claim 51, wherein step (a) comprises applying tension to the nucleic acid.

63. A method of performing nucleic acid amplification, comprising:
   (a) denaturing a double-stranded nucleic acid to produce single-stranded template strands;
   (b) annealing primers to the template strands;
   (c) extending the primers by a template-strand-driven polymerase to produce extension products while applying mechanical tension to the primer or the template strands, thereby forming double-stranded nucleic acid molecules; and
   (d) repeating steps (a)-(c) to amplify the double-stranded nucleic acid,
      wherein at least one of the double-stranded nucleic acid molecules produced in step (c) in a cycle, of steps (a)-(c) is denatured in step (a) in a subsequent cycle of steps (a)-(c), so that at least one extension product formed in step (c) is used as a template strand in a subsequent cycle of steps (a)-(d).

64. A method of performing nucleic acid amplification, comprising:
   (a) denaturing a double-stranded nucleic acid to produce single-stranded template strands;
   (b) annealing primers to the template strands;
   (c) extending the primers by a template-strand-driven polymerase to produce extension products, thereby forming double- stranded nucleic acid molecules; and
   (d) repeating steps (a)-(c) to amplify the double-stranded nucleic acid,
      wherein at least one of the double-stranded nucleic acid molecules produced in step (c) in a cycle of steps (a)-(c) is denatured in step (a) in a subsequent cycle of steps (a)-(c), so that at least one extension product formed in step (c) is used as a template strand in a subsequent cycle of steps (a)-(d), and
      wherein at least one of steps (a)-(c) comprises applying hydrodynamic tension to the nucleic acid.

65. A method of performing nucleic acid amplification, comprising:
   (a) denaturing a double-stranded nucleic acid to produce single-stranded template strands;
   (b) annealing primers to the template strands;
   (c) extending the primers by a template-strand-driven polymerase to produce extension products while applying electromagnetic tension to the primer or the template strands, thereby forming double-stranded nucleic acid molecules; and
   (d) repeating steps (a)-(c) to amplify the double-stranded nucleic acid,
      wherein at least one of the double-stranded nucleic acid molecules produced in step (c) in a cycle of steps (a)-(c) is denatured in step (a) in a subsequent cycle of steps (a)-(c), so that at least one extension product formed in step (c) is used as a template strand in a subsequent cycle of steps (a)-(d).

66. The method of claim 65, wherein step (a) or step (b) comprises applying electromagnetic tension to the nucleic acid.

67. A method of performing nucleic acid amplification, comprising:
   (a) denaturing a double-stranded nucleic acid to produce single-stranded template strands;
   (b) annealing primers to the template strands;
   (c) extending the primers by a template-strand-driven polymerase to. produce extension products, thereby forming double-stranded nucleic acid molecules; and
   (d) repeating steps (a)-(c) to amplify the double-stranded nucleic acid, wherein step (a) is isothermal and comprises applying mechanical or hydrodynamic tension to the nucleic acid;

and wherein at least one of the double-stranded nucleic acid molecules produced in step (c) in a cycle of steps (a)-(c) is denatured in step (a) in a subsequent cycle of steps (a)-(c), so that at least one extension product formed in step (c) is used as a template strand in a subsequent cycle of steps (a)-(d).

68. The method of claim 67, wherein steps (b) through (c) are isothermal.

69. A method of performing nucleic acid amplification, comprising:
(a) denaturing a double-stranded nucleic acid to produce single-stranded template strands;
(b) annealing primers to the template strands;
(c) extending the primers by a template-strand-driven polymerase to produce extension products, thereby forming double- stranded nucleic acid molecules; and
(d) repeating steps (a)-(c) to amplify the double-stranded nucleic acid,
wherein at least one of the extension products in step (c) is used as a template strand in a subsequent cycle of steps (a)-(d), and
wherein step (c) comprises applying adjustable tension that tends to stretch the nucleic acid to the nucleic acid, said adjustable tension modulating proofreading exonuclease activity of the nucleic acid polymerase.

70. A method of performing nucleic acid amplification, comprising:
(a) denaturing a double-stranded nucleic acid to produce single-stranded template strands;
(b) annealing primers to the template strands;
(c) extending the primers by a template-strand-driven polymerase to produce extension products, thereby forming double-stranded nucleic acid molecules; and
(d) repeating steps (a)-(c) to amplify the double-stranded nucleic acid,
wherein at least one extension product in step (c) is used as a template strand in a subsequent cycle of steps (a)-(c), and
wherein primers used in step (b) are activatable primers comprising complexing groups for immobilizing extension products obtained in step (c) wherein tension that tends to stretch the nucleic acid is applied in at least one cycle.

71. A method of performing nucleic acid amplification, comprising:
(a) denaturing a double-stranded nucleic acid to produce single-stranded template strands;
(b) annealing primers to the template strands;
(c) extending the primers by a template-strand-driven polymerase to produce extension products, thereby forming double-stranded nucleic acid molecules; and
(d) repeating steps (a)-(c) to amplify the double-stranded nucleic acid,
wherein at least one extension product in step (c) is used as a template strand in a subsequent cycle of steps (a)-(c), and
wherein at least one of steps (a)-(c) comprises applying tension that tends to stretch the nucleic acid to the nucleic acid; and
wherein primers used in step (b) are activatable primers comprising complexing groups for immobilizing extension products obtained in step (c).

72. The method of claim 71, wherein the tension applied during at least one of steps (a)-(c) is mechanical tension.

73. A method of performing nucleic acid amplification, comprising:
(a) denaturing a double-stranded nucleic acid to produce single-stranded template strands;
(b) annealing primers to the template strands; and
(c) extending the primers by a template-strand-driven polymerase to produce extension products, thereby forming double-stranded nucleic acid molecules; and
(d) repeating steps (a)-(c) to amplify the double-stranded nucleic acid,
wherein at least one of the double-stranded nucleic acid molecules produced in step (c) in a cycle of steps (a)-(c) is denatured in step (a) in a subsequent cycle of steps (a)-(c), so that at least one extension product formed in step (c) is used as a template strand in a subsequent cycle of steps (a)-(d),
wherein at least one of steps (b) and (c) comprises applying tension that tends to stretch the nucleic acid to the nucleic acid, and
wherein the number of copies of the template strand increases exponentially, as a power of n, after steps (a) through (c) are repeated n times, wherein n is an integer greater than 1.

74. A method for controlling the stringency of annealing of a primer to a nucleic acid template strand, comprising:
in a plurality of cycles of nucleic acid amplification,
annealing a primer to a nucleic acid template strand, wherein tension that tends to stretch the nucleic acid is adjustably applied to said nucleic acid template strand or to said primer to control the stringency of annealing of said primer to said nucleic acid template strand; and
wherein an extension product formed by extending the primer by a nucleic acid polymerase is used as a nucleic acid template strand in a subsequent cycle of nucleic acid amplification.

75. A method for lowering the error rates of extending a primer by a nucleic acid polymerase, comprising:
in a plurality of cycles of nucleic acid amplification,
extending a primer annealed to a nucleic acid template strand by a nucleic acid polymerase to produce an extension product comprising double-stranded nucleic acid molecules, wherein tension that tends to stretch the nucleic acid is adjustably applied to said nucleic acid template strand or to said primer to lower the error rates of extending said primer by nucleic acid polymerase, wherein the extension product is used as a nucleic acid template strand in a subsequent cycle of nucleic acid amplification.

76. A method for controlling the stringency of annealing of a primer to a GC-rich nucleic acid template strand, comprising:
in a plurality of cycles of nucleic acid amplification,
annealing a primer to a GC-rich nucleic acid template strand, wherein tension that tends to stretch the nucleic acid is adjustably applied to said GC-rich nucleic acid template strand or to said primer to control the stringency of annealing of said primer to said GC-rich nucleic acid template strand; and
wherein an extension product formed by a nucleic acid polymerase is used as a nucleic acid template strand in a subsequent cycle of nucleic acid amplification.

77. A method for lowering the error rates of extending a primer on a GC-rich template strand by a nucleic acid polymerase, comprising:
in a plurality of cycles of nucleic acid amplification,
extending a primer annealed to a GC-rich nucleic acid template strand by a nucleic acid polymerase to produce an extension product comprising double-stranded nucleic acid molecules, wherein tension that tends to stretch the nucleic acid is adjustably applied to said GC-rich nucleic acid template strand or to said primer to lower the error rates of extending said primer on said GC-rich nucleic acid template strand, wherein the extension product is used as a nucleic acid template strand in a subsequent cycle of nucleic acid amplification.

78. A method of improving fidelity of nucleic acid amplification, comprising:
 (a) denaturing a double-stranded nucleic acid to produce single-stranded template strands;
 (b) annealing primers to the template strands; and
 (c) extending the primers by a template-strand-driven polymerase to produce extension products, thereby forming double-stranded nucleic acid molecules; and
 (d) repeating steps (a)-(c) to amplify the double-stranded nucleic acid,
  wherein at least one of the double-stranded nucleic acid molecules produced in step (c) in a cycle of steps (a)-(c) is denatured in step (a) in a subsequent cycle of steps (a)-(c), so that at least one extension product formed in step (c) is used as a template strand in a subsequent cycle of steps (a)-(d), and
  wherein at least one of steps (a) through (c) comprises adjustably applying tension that tends to stretch the nucleic acid to the nucleic acid to improve fidelity of nucleic acid amplification.

79. A method for amplifying a nucleic acid, comprising:
 (a) contracting one or more template strands of single-stranded nucleic acid with one or more oglinucleotide primers complementary to a portion of the one or more template strands;
 (b) annealing at least one primer of the one or more primers to the portion of the one or more template strands to which the primer is complementary;
 (c) contacting the one or more template strands with a nucleic acid polymerase and at least four different nucleoside triphosphates;
 (d) extending the at least one annealed primer by the nucleic acid polymerase while applying mechanical tension, hydrodynamic tension, or electromagnetic tension to the one or more primer or the one or more template strands, thereby forming one or more extension products bound to the one or more template strands, wherein mechanical tension, hydrodynamic tension, or electromagnetic tension tends to stretch the nucleic acid;
 (e) separating the one or more extension products from the one or more template strands; and
 (f) repeating steps (a)-(e) to amplify the nucleic acid,
 wherein at least one of the one or more extension products in step (e) is used as template strands in a subsequent cycle of steps (a)-(e), wherein, for the last cycle, step (e) is optional.

80. A method for amplifying nucleic acid, comprising:
 (a) contacting one or more template strands of single-stranded nucleic acid with one or more oligonucleotide primers complementary to a portion of the one or more template strands;
 (b) annealing at least one primer of the one or more primers to the portion of the one or more template strands to which the primer is complementary;
 (c) contacting the one or more template strands with a nucleic acid polymerase and at least four different nucleoside triphosphates;
 (d) extending the at least one annealed primer by the nucleic acid polymerase thereby forming one or more extension products bound to the one or more template strands;
 (e) separating the one or more extension products from the one or more template strands; and
 (f) repeating steps (a)-(e) to amplify the nucleic acid,
 wherein at least one of the one or more extension products in step (e) is used as template strands in a subsequent cycle of steps (a)-(e),
 wherein, for the last cycle, step (e) is optional, and
 wherein at least one of steps (a)-(e) comprises applying hydrodynamic tension to the one or more template strands.

81. A method for amplifying a nucleic acid, comprising:
 (a) contacting one or more template strands of single-stranded nucleic acid with one or more oligonucleotide primers complementary to a portion of the one or more template strands;
 (b) annealing at least one primer of the one or more primers to the portion of the one or more template strands to which the primer is complementary;
 (c) contacting the one or more template strands with a nucleic acid polymerase and at least four different nucleoside triphosphates;
 (d) extending the at least one annealed primer by the nucleic acid polymerase, thereby forming one or more extension products bound to the one or more template strands;
 (e) separating the one or more extension products from the one or more template strands; and
 (f) repeating steps (a)-(e) to amplify the nucleic acid,
 wherein at least one of the one or more extension products in step (e) is used as template strands in a subsequent cycle of steps (a)-(e),
 wherein, for the last cycle, step (e) is optional, and
 wherein tension that tends to stretch the nucleic acid is applied and varied during each cycle of steps (a)-(e).

82. A method for amplifying a nucleic acid, comprising:
 (a) contacting one or more template strands of single-stranded nucleic acid with one or more oligonucleotide primers complementary to a portion of the one or more template strands;
 (b) annealing at least one primer of the one or more primers to the portion of the one or more template strands to which the primer is complementary;
 (c) contacting the one or more template strands with a nucleic acid polymerase and at least four different nucleoside triphosphates;
 (d) extending the at least one annealed primer by the nucleic acid polymerase, thereby forming one or more extension products bound to the one or more template strands;
 (e) separating the one or more extension products from the one or more template strands; and
 (f) repeating steps (a)-(e) to amplify the nucleic acid,
 wherein at least one of the one or more extension products in step (e) is used as template strands in a subsequent cycle of steps (a)-(e),
  wherein, for the last cycle, step (e) is optional,
  wherein tension that tends to stretch the nucleic acid is applied and varied during each cycle of steps (a)-(e), and
  wherein each step (a) through (e) is isothermal.

* * * * *

UNITED STATES PATENT AND TRADEMARK OFFICE
CERTIFICATE OF CORRECTION

PATENT NO. : 7,494,791 B2  Page 1 of 1
APPLICATION NO. : 11/128301
DATED : February 24, 2009
INVENTOR(S) : Anita Goel It is certified that error appears in the above-identified patent and that said Letters Patent is hereby corrected as shown below:

<u>Claim 48, Column 27, Line 8</u>

Delete "." after the symbols "20° C".

<u>Claim 67, Column 28, Line 64</u>

Delete "." after the word "to".

<u>Claim 79, Column 31, Line 31</u>

Delete "contracting" and insert --contacting--.

<u>Claim 79, Column 31, Line 32</u>

Delete "oglinucleotide" and insert --oligonucleotide--.

Signed and Sealed this

Twenty-eighth Day of July, 2009

JOHN DOLL
*Acting Director of the United States Patent and Trademark Office*